United States Patent [19]

Behnke et al.

[11] Patent Number: 5,351,383
[45] Date of Patent: Oct. 4, 1994

[54] METHOD OF MAKING AN INJECTION OR SAMPLING SITE

[75] Inventors: Brett A. Behnke, Hastings; Gary A. Thill, White Bear Lake, both of Minn.

[73] Assignee: Minnesota Mining and Manufacturing Company, St. Paul, Minn.

[21] Appl. No.: 43,466

[22] Filed: Apr. 2, 1993

Related U.S. Application Data

[63] Continuation-in-part of Ser. No. 921,908, Jul. 29, 1992, Pat. No. 5,300,034.

[51] Int. Cl.⁵ .............................. B21D 39/03
[52] U.S. Cl. ...................... 29/430; 29/511; 29/516; 29/520; 264/154; 83/30
[58] Field of Search .......... 29/432, 450, 451, 511, 29/516, 520, 430, 650; 264/154, 229; 83/30

[56] References Cited

U.S. PATENT DOCUMENTS

| | | |
|---|---|---|
| 1,180,665 | 4/1916 | McElroy . |
| 2,436,291 | 2/1948 | Daniel . |
| 2,546,672 | 3/1951 | LeClair . |
| 2,579,725 | 12/1951 | Breakstone . |
| 2,998,635 | 9/1961 | Burritt, Jr. et al. ............ 29/511 |
| 3,057,350 | 10/1962 | Cowley . |
| 3,313,299 | 4/1967 | Spademan . |
| 3,332,418 | 7/1967 | Brody . |
| 3,376,866 | 4/1968 | Ogle . |
| 3,729,031 | 4/1973 | Baldwin . |
| 3,729,032 | 4/1973 | Tischlinger et al. . |
| 3,776,229 | 12/1973 | McPhee . |
| 3,853,127 | 12/1974 | Spademan . |
| 3,976,073 | 8/1976 | Quick et al. . |
| 3,977,400 | 8/1976 | Moorehead . |
| 3,986,508 | 10/1976 | Barrington . |

(List continued on next page.)

FOREIGN PATENT DOCUMENTS

| | | |
|---|---|---|
| 13945 | 10/1971 | Australia . |
| 964544 | 3/1975 | Canada . |
| 1043744 | 12/1978 | Canada . |
| 1215945 | 12/1986 | Canada . |
| 0157224 | 3/1985 | European Pat. Off. . |
| 0344907 | 12/1989 | European Pat. Off. . |
| 0324839 | 8/1991 | European Pat. Off. . |
| 0495330 | 7/1992 | European Pat. Off. . |
| 35387 | 11/1965 | Fed. Rep. of Germany . |
| 8425197.2 | 10/1985 | Fed. Rep. of Germany . |
| WO89/06553 | 7/1989 | PCT Int'l Appl. . |
| WO90/12606 | 11/1990 | PCT Int'l Appl. . |
| WO91/05581 | 5/1991 | PCT Int'l Appl. . |
| WO91/07206 | 5/1991 | PCT Int'l Appl. . |
| WO91/10459 | 7/1991 | PCT Int'l Appl. . |
| WO92/04936 | 4/1992 | PCT Int'l Appl. . |
| 1078650 | 8/1967 | United Kingdom . |
| 2033230 | 5/1980 | United Kingdom . |
| 2067075 | 11/1983 | United Kingdom . |

OTHER PUBLICATIONS

Special Report and Product Review "Needlestick-Prevention Devices"; Health Devices, May 1991, vol. 20, No. 5, pp. 154–181.
Article entitled "I.V. Sets and Solutions SafeLine No-Needle I.V. System" by Kendall McCaw Laboratories Inc., 1990.
1991 Annual Report of Becton Dickinson.
Leaflet showing filling instruction for Ped-Pod Oral Dispenser and Ny-Pod Hypodermic Sryinge; SoloPak Laboratories, Elk Grove Village, Illinois.
Brochure entitled "IMED Needleless System"; by IMED Corporation, 1993.

*Primary Examiner*—Mark Rosenbaum
*Assistant Examiner*—David P. Bryant
*Attorney, Agent, or Firm*—Gary L. Griswold; Walter N. Kirn; Stephen W. Bauer

[57] ABSTRACT

A method of making an injection and sampling site adapted to receive a blunt cannula. The method comprises providing an elastomeric septum, and a housing adapted to receive that septum; making a slit in the elastomeric septum; inserting the elastomeric septum into the passageway of the housing; and swaging an outer annular ledge on the housing inwardly over the septum until a septum-engaging portion of the swaging tool applies a predetermined amount of force to the septum. Before the swaging step, a pin is inserted into the passageway of the housing against the inside end of the septum to inhibit deformation of the septum during swaging.

54 Claims, 7 Drawing Sheets

U.S. PATENT DOCUMENTS

| | | | |
|---|---|---|---|
| 3,990,445 | 11/1976 | Lundquist . | |
| 3,995,630 | 12/1976 | van de Veerdonk . | |
| 4,000,739 | 1/1977 | Stevens . | |
| 4,000,740 | 1/1977 | Mittleman . | |
| 4,048,995 | 9/1977 | Mittleman . | |
| 4,048,996 | 9/1977 | Mittleman et al. . | |
| 4,133,441 | 1/1979 | Mittleman et al. . | |
| 4,134,512 | 1/1979 | Nugent . | |
| 4,197,848 | 4/1980 | Garrett et al. . | |
| 4,219,912 | 9/1980 | Adams . | |
| 4,236,880 | 12/1980 | Archibald . | |
| 4,259,276 | 3/1981 | Rawlings | 264/154 |
| 4,277,226 | 7/1981 | Archibald . | |
| 4,289,129 | 9/1981 | Turner . | |
| 4,294,249 | 10/1981 | Sheehan et al. . | |
| 4,303,067 | 12/1981 | Connolly et al. . | |
| 4,322,201 | 3/1982 | Archibald . | |
| 4,405,316 | 9/1983 | Mittleman . | |
| 4,411,662 | 10/1983 | Pearson . | |
| 4,412,573 | 11/1983 | Zbed . | |
| 4,416,661 | 11/1983 | Norman et al. . | |
| 4,424,833 | 1/1984 | Spector et al. . | |
| 4,434,822 | 3/1984 | Bellamy et al. . | |
| 4,475,548 | 10/1984 | Muto . | |
| 4,496,348 | 1/1985 | Genese et al. . | |
| 4,511,359 | 4/1985 | Vaillancourt . | |
| 4,578,063 | 3/1986 | Inman et al. . | |
| 4,610,469 | 9/1986 | Wolff-Mooij . | |
| 4,610,665 | 9/1986 | Matsumoto et al. . | |
| 4,610,674 | 9/1986 | Suzuki et al. . | |
| 4,626,245 | 12/1986 | Weinstein . | |
| 4,637,817 | 1/1987 | Archibald et al. . | |
| 4,673,390 | 6/1987 | Archibald . | |
| 4,673,393 | 6/1987 | Suzuki et al. . | |
| 4,675,020 | 6/1987 | McPhee . | |
| 4,705,506 | 11/1987 | Archibald . | |
| 4,714,463 | 12/1987 | Archibald et al. . | |
| 4,723,550 | 2/1988 | Bales et al. . | |
| 4,735,311 | 4/1988 | Lowe et al. | 29/511 |
| 4,752,292 | 6/1988 | Lopez et al. . | |
| 4,768,568 | 9/1988 | Fournier et al. . | |
| 4,781,680 | 11/1988 | Redmond et al. . | |
| 4,798,594 | 1/1989 | Hillstead . | |
| 4,804,366 | 2/1989 | Zdeb et al. . | |
| 4,809,679 | 3/1989 | Shimonaka et al. . | |
| 4,857,062 | 8/1989 | Russell . | |
| 4,874,369 | 10/1989 | Kulle et al. . | |
| 4,874,378 | 10/1989 | Hillstead . | |
| 4,886,495 | 12/1989 | Reynolds . | |
| 4,889,256 | 12/1989 | Fowies . | |
| 4,892,222 | 1/1990 | Schmidt et al. . | |
| 4,895,346 | 1/1990 | Steigerwald . | |
| 4,932,633 | 6/1990 | Johnson et al. . | |
| 4,935,010 | 6/1990 | Cox et al. . | |
| 4,950,260 | 8/1990 | Bonaldo . | |
| 5,009,391 | 4/1991 | Steigerwald . | |
| 5,017,192 | 5/1991 | Dodge et al. . | |
| 5,071,404 | 12/1991 | Larkin et al. . | |
| 5,078,948 | 1/1992 | Troutman et al. | 264/154 |
| 5,080,654 | 1/1992 | Picha et al. . | |
| 5,088,984 | 2/1992 | Fields . | |
| 5,088,995 | 2/1992 | Packard et al. . | |
| 5,100,394 | 3/1992 | Dudar et al. . | |
| 5,114,408 | 5/1992 | Fleischhaker et al. . | |
| 5,135,489 | 8/1992 | Jepson et al. . | |
| 5,149,327 | 9/1992 | Oshiyama . | |
| 5,167,648 | 12/1992 | Jepson et al. . | |
| 5,171,234 | 12/1992 | Jepson et al. . | |
| 5,188,620 | 2/1993 | Jepson et al. . | |
| 5,199,947 | 4/1993 | Lopez et al. . | |
| 5,199,948 | 4/1993 | McPhee . | |
| 5,201,725 | 4/1993 | Kling . | |
| 5,203,775 | 4/1993 | Frank et al. . | |
| 5,211,634 | 5/1993 | Vaillancourt . | |
| 5,211,638 | 5/1993 | Dudar et al. . | |
| 5,215,537 | 6/1993 | Lynn et al. . | |
| 5,279,571 | 1/1994 | Larkin | 604/167 |

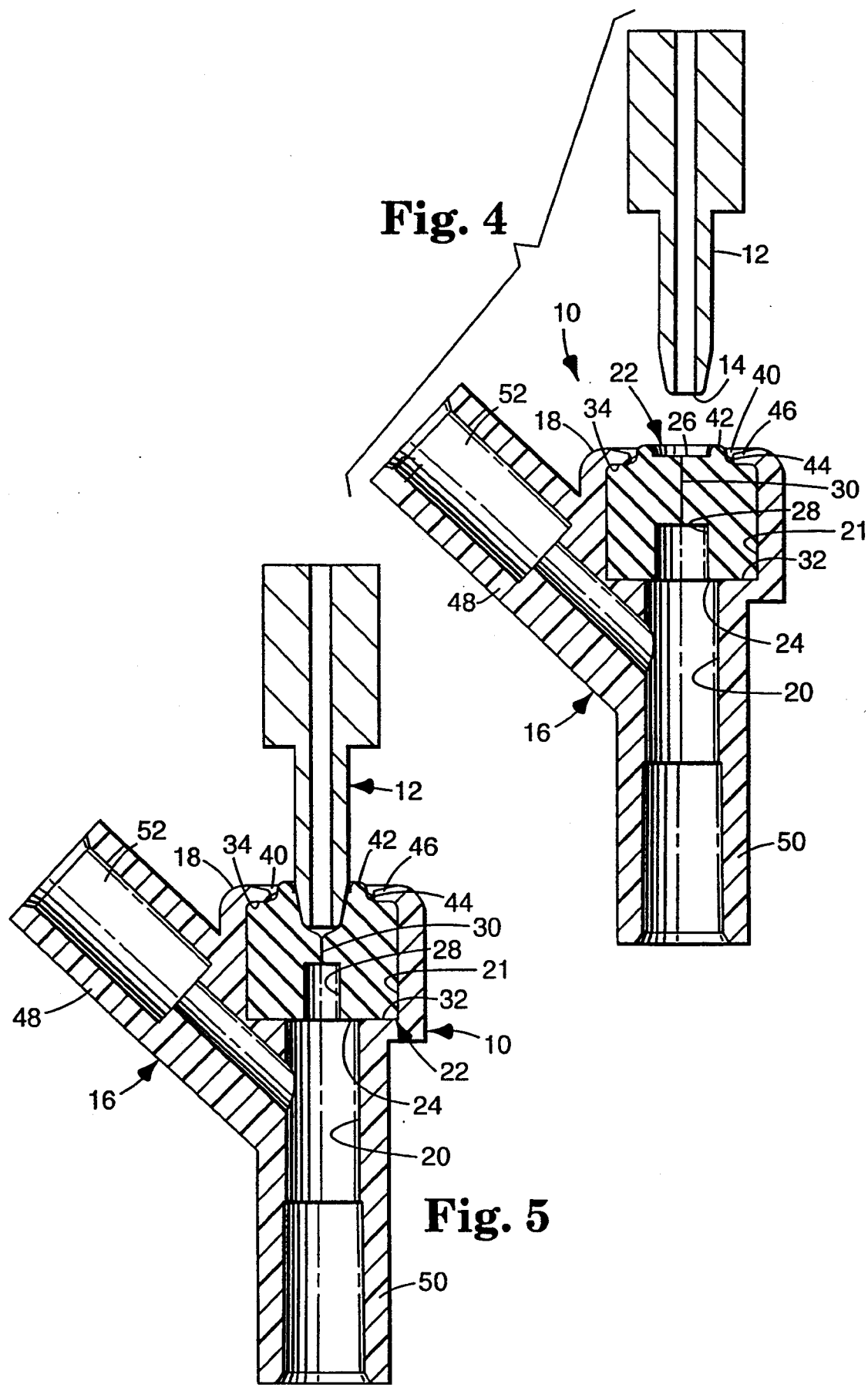

METHOD OF MAKING AN INJECTION OR SAMPLING SITE

This application is a continuation-in-part of U.S. patent application Ser. No. 07/921,908, filed Jul. 29, 1992, now U.S. Pat. No. 5,300,034.

BACKGROUND OF THE INVENTION

This invention relates generally to infusion therapy and IV injection or sampling sites, and more particularly to apparatus for and method of making an injection or sampling site, such as an IV injection site, adapted for use with a blunt cannula.

In an effort to reduce the risk of transmitting infectious diseases, such as hepatitis and AIDS, via accidental needle sticks, various designs of IV injection sites have been developed that are adapted to receive a blunt cannula and/or shielded cannula. See, e.g., Special Report and Product Review, Needlestick-Prevention Devices, Health Devices, pages 154–180 (ECRI, Plymouth Meeting, Penn. 1991). One approach has been to employ a slit septum Y-site in which a slit elastomeric septum is compressed in the Y-site housing. A blunt cannula can be introduced through the slit of the septum, and assuming the design works as intended, the septum will seal against the cannula shaft. When the cannula is removed, the septum seals itself.

Injection sites of this type are either available from or publicized by Baxter International, Inc., Deerfield, Ill., under the trade designation "Baxter's Needle-Less Injection Sites"; Abbott Laboratories, Inc., Abbott Park, Ill., under the trade designation "LifeShield Infection Control System"; and Kendall McGaw Laboratories, Inc., Irvine, Calif., under the trade designation "Safe-Line No-Needle I.V. System". A blunt cannula has been available from Becton, Dickinson and Company, Paramus, N.J., under the trade designation "Interlink System".

One problem with these systems is that they are sometimes incompatible. Some slit septum systems have permitted leakage either when a cannula is inserted or when no cannula has been inserted. In at least one slit septum site, it is possible to upset the septum in its housing by using an unspecified cannula or attempting to insert the cannula through the material of the septum somewhere other than through the slit.

Another problem with slit septum systems is inconsistent resistance to being pierced with a blunt cannula. Injection sites of the same system will require the medical practitioner to exert widely varying amount of force before the blunt cannula will pierce the septum.

SUMMARY OF THE INVENTION

This invention provides an apparatus for and method of making an injection or sampling site, such as an IV injection Y-site on an IV tubing set, adapted to receive a blunt cannula. The apparatus and method provide improved process consistency compared to prior methods, and lower and more consistent penetration forces when a blunt cannula is inserted in the IV injection site made according to the method. The apparatus and method also provide a relatively economical means for making injection or sampling sites.

Generally, the method according to the invention is performed on a housing having an outside end and a passageway extending inwardly from the outside end, the passageway opening through the outside end and defining a longitudinal direction, and an elastomeric septum having an outside end corresponding to the outside end of the housing and an inside end opposite its outside end. In one aspect of the method, the elastomeric septum is inserted into the passageway of the housing; a pin is inserted into the passageway of the housing to engage the inside end of the septum to reduce or prevent expansion of the septum inwardly through the passageway when the outer end of the housing is swaged; and the outside end of the housing is swaged inwardly over the septum with a swaging tool during or after insertion of the pin.

Preferably, the swaging process is stopped when the swaging tool applies a predetermined amount of force to the septum. The swaging tool preferably has a septum-engaging portion and a housing-swaging portion, and the septum is engaged with the septum-engaging portion of the swaging tool before stopping the swaging process.

Most preferably, the septum has a bore extending part-way through the septum from the inside end of the septum, and the pin is also inserted into the bore of the septum.

Accordingly, in its first aspect, the invention facilitates fabricating an injection or sampling site in which the housing is swaged without longitudinal compression of the septum. By preventing deformation of the septum during the swaging process with the swaging tool, pin and the walls of the housing, longitudinal compression is also prevented. This is because the elastomeric material of the septum is incompressible. The resulting injection or sampling site is believed to provide more consistent penetration force required to pierce the septum with a blunt cannula.

In another aspect of the method of the invention, the a slit is cut into an elastomeric septum. The method may be performed with an apparatus for slitting the septum, which apparatus comprises a block having a septum-receiving bore, a back support for supporting one end of the septum, and a knife. The septum is inserted into the septum-receiving bore against the back support, with the septum-receiving bore laterally or radially capturing the septum to prevent radial deformation of the septum. A slit is then cut into the septum with a knife, with the knife being aligned with the septum-receiving bore and the septum captured in the bore such that the slit is aligned with respect to the septum. After cutting the slit into the septum, the septum is removed from the septum-receiving bore. During or after removal of the septum from the septum-receiving bore, the septum is inserted into a housing of an injection or sampling site.

Accordingly, in one aspect of the method of the invention, the septum is held in a septum-receiving bore and prevented from deforming laterally or radially while a slit is cut into the septum with a knife. As a result, the knife is able to cut a precisely aligned or centered slit through the septum. This is accomplished on a consistent basis.

In one preferred version, the method comprises first slitting the septum according to the slitting method described above, loading the slit septum into a housing, and swaging the outside end of the housing inwardly over the septum according to the swaging method described above.

The apparatus of the invention, in one aspect, generally comprises pin means, swaging means and means for stopping the swaging means. The pin means is adapted to reduce or prevent expansion of the septum inwardly through the passageway when the outer end of the housing is swaged. The pin means is inserted into the passageway of a housing into engagement with the inside end of a septum inserted into the passageway. The swaging means swages the outside end of the housing inwardly over the septum. The means for stopping the swaging means stops the swaging means from further swaging of the housing when the swaging means applies a predetermined amount of force to the septum.

Preferably, the swaging means comprises a swaging tool having a septum-engaging portion and a housing-swaging portion. The septum-engaging portion and housing-swaging portion are configured, and the means for stopping the swaging means is adapted, to stop the swaging process before the outside end of the housing applies longitudinal compression to the septum.

In another aspect, the apparatus of the invention generally comprises a block, a back support, a knife, and pushing means. The block has a septum-receiving bore for receiving a septum before it is inserted into a housing, with the septum-receiving bore laterally or radially constraining the septum to prevent lateral or radial deformation of the septum. The back support supports one end of the septum received in the septum-receiving bore of the block. The knife is movable relative to the septum-receiving bore of the block to cut a slit into a septum received in the septum-receiving bore. The pushing means removes the septum from the septum-receiving bore and inserts the septum into the passageway of a housing.

Preferably, the septum-receiving bore has a diameter substantially equal to the diameter of a housing into which a septum will be inserted.

Most preferably, the slitting apparatus and the swaging apparatus are combined into one apparatus that slits the septum and swages the housing. The apparatus conveniently comprises two turntables, the first of which holds septums for slitting, and the second of which holds housings into which the slit septums are transferred before the housings are swaged.

For example, the first turntable (also constituting the block) has a plurality of septum-receiving bores, and is mounted for rotation relative to the back support to move the septum-receiving bores relative to the back support between slitting and unloading stations. At the unloading station, the back support has a passageway sized to allow a septum received in the septum-receiving bore to be pushed through the passageway by the pushing means. The septum-receiving bore of the first turntable at the slitting station is not adjacent the passageway of the back support.

The second turntable has a plurality of housing-receiving openings for receiving the housing of the injection or sampling site, and is rotatable to move the housing-receiving openings between a septum-loading station and a swaging station. At the septum-loading station, a housing-receiving opening is aligned with the passageway of the back support to enable a septum to be loaded into a housing received in that housing-receiving opening. At the swaging station, the housing-receiving opening is aligned with the swaging means to enable the swaging means to swage the outside end of a housing received in that housing-receiving opening.

Most preferably, a means is provided for controlling the knife, pushing means and swaging means to substantially simultaneously (a) cut a septum received in the septum-receiving bore at the slitting station with the knife, (b) push a septum received in the septum-receiving bore at the unloading station of the first turntable with the pushing means into a housing received in a housing-receiving opening at the septum-loading station of the second turntable, and (c) swage the end of a housing inwardly over the septum at the swaging station with the swaging means. For example, the means for controlling the knife, pushing means and swaging means may comprise pneumatic means for moving the knife, pushing means and swaging means through their operative range of motion.

Other features will be pointed out hereinafter.

BRIEF DESCRIPTION OF THE DRAWING

The invention will be further described with reference to the drawing wherein corresponding reference characters indicate corresponding parts throughout the several views of the drawing, and wherein:

FIG. 4 is an enlarged cross-sectional view of the IV injection site of FIGS. 1 and 2 and a blunt cannula, showing the IV injection site before the cannula has been introduced therein;

FIG. 5 is an enlarged cross-sectional view of the IV injection site and cannula of FIG. 4, showing the cannula partly inserted into the injection site;

DETAILED DESCRIPTION OF PREFERRED EMBODIMENTS

1. IV Injection Site

Figure 6:
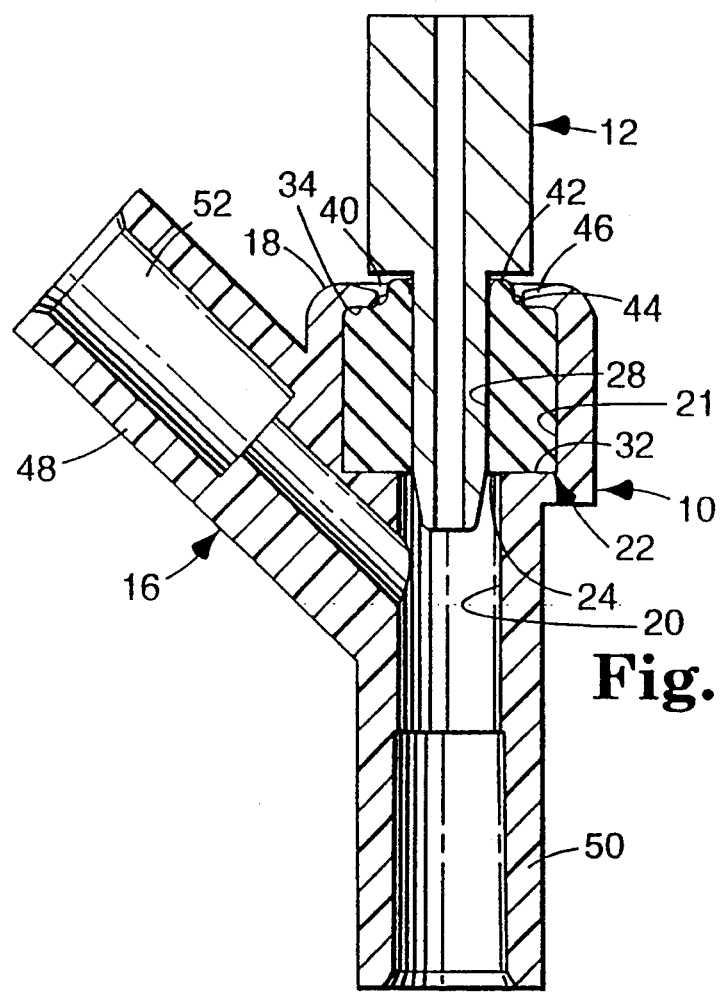
FIG. 6 is an enlarged cross-sectional view of the IV injection site and cannula of FIGS. 4 and 5, showing the cannula substantially completely inserted into the injection site.

Now referring to the drawing, a preferred IV injection site made with the apparatus and method of the invention is designated in its entirety by the reference numeral 10. The IV injection site 10 may be of the general type known as a Y-site, which provides a sealed port for injecting fluids into an IV tubing set (not shown). It is contemplated that the injection site 10 could be used in such IV administration tubing sets, drug vials, or other fluid systems involving medical fluids or a medical setting. The injection site 10 is particularly designed to be used with a blunt plastic or metal cannula 12 (FIGS. 4-6) that has a relatively smooth end 14 to reduce the risk to medical personnel of accidental needle sticks.

The injection site 10 generally comprises a housing 16 having an outside end 18 and a passageway 20 extending inwardly from the outside end 18. The passageway 20 defines a longitudinal direction. An elastomeric septum 22 is closely received in the passageway 20 of the housing 16. The septum 22 has inside and outside ends 24 and 26 relative to the outside end 18 of the housing 16. A bore 28 extends into the septum 22 from the inside end 24 of the septum 22 generally in the longitudinal direction but not through the septum 22, and a slit 30 extends generally in the longitudinal direction into the septum 22 from the outside end 26 of the septum 22 to the bore 28.

The arrangement is such that, when a cannula 12 is introduced through the slit 30 of the septum 22, the elastomeric material of the septum 22 expands into the bore 28 of the septum 22 to sealingly engage the cannula 12 along the bore 28 of the septum 22.

The housing 16 includes opposed inner and outer annular ledges 32 and 34 defining a septum-receiving portion 21 of the passageway 20. The inner ledge 32 engages the inside end 24 of the septum 22 adjacent the periphery thereof, and the outer ledge 34 engages the outside end 26 of the septum 22 adjacent the periphery thereof. The septum-receiving portion 21 of the passageway 20 is generally cylindrical.

Figure 2:
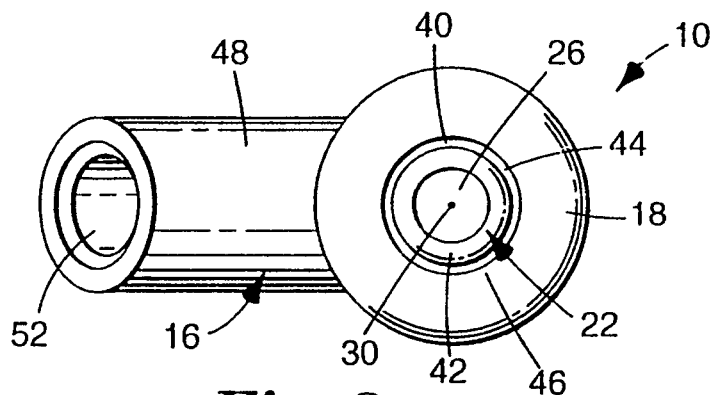
FIG. 2 is a top plan view of the IV injection site of FIG. 1.
Figure 1:
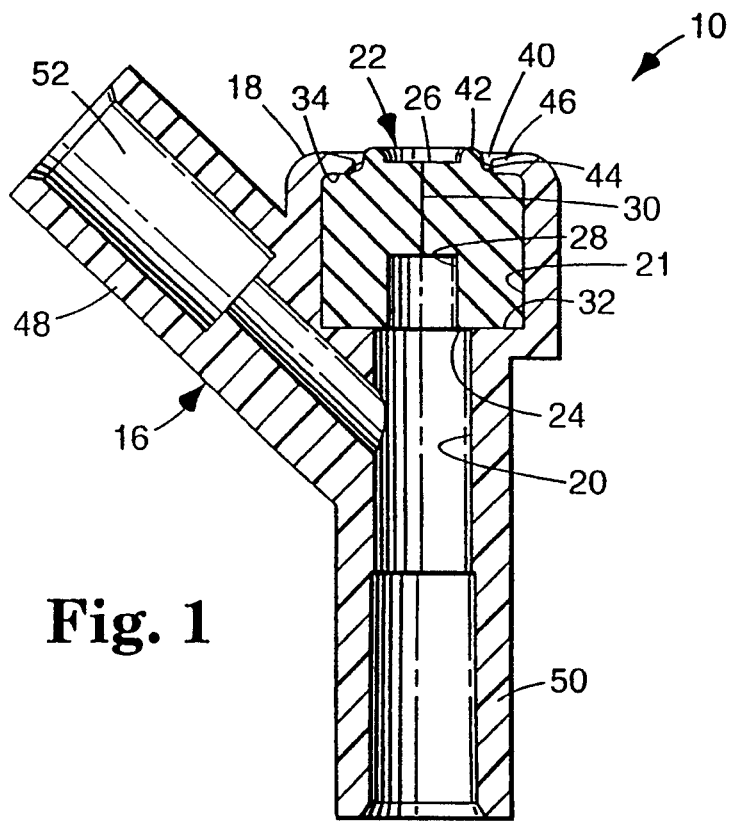
FIG. 1 is an enlarged cross-sectional view of the IV injection site, showing a novel septum and housing design.
Figure 3:
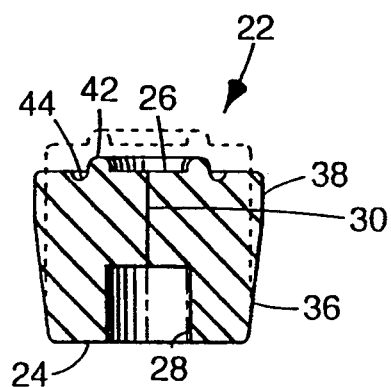
FIG. 3 is a cross-sectional view of the septum of FIG. 1, illustrating its configuration before it is assembled in the housing of the IV injection site.

Preferably, the septum 22 is formed, before being inserted in the housing 16 during assembly of the IV injection site 10, in a combined frustoconical/cylindrical configuration as illustrated in FIG. 3. The pre-assembly septum 22 includes a generally frustoconical portion 36 adjacent the inside end 24 of the septum 22 and tapering downwardly in the direction toward the inside end 24, and a generally constant diameter cylindrical portion 38 extending from the frustoconical portion 36 to the outside end 26 of the septum 22. The septum 22 is compressed radially by the housing 16 so as to have a generally cylindrical configuration after the septum 22 has been inserted in the housing 16 during assembly of the IV injection site 10.

Most preferably, the bore 28 of the septum 22 extends between 25-50% through the septum 22 and the slit 30 of the septum 22 extends between 50-75% through the septum 22, and the frustoconical portion 36 of the septum 22 extends a greater distance from the inside end 24 of the septum 22 than the bore 28 extends from the inside end 24 of the septum 22. As an illustrative example of the pre-assembly dimensions of the septum 22, the bore 28 may have a depth of approximately 0.105 inches (2.7 mm); the slit 30 may have a depth (longitudinally along the septum 22) of approximately 0.129 inches (3.3 mm); the frustoconical portion 36 may have a length of approximately 0.164 inches (4 mm); and the cylindrical portion 38 may have a length of approximately 0.070 inches (1.8 mm). These dimensions change somewhat when the septum 22 is inserted into the housing 16 during assembly of the injection site 10.

The septum-receiving portion 21 of the passageway 20, which is defined as that portion 21 between the inner and outer ledges 32 and 34, is defined by a generally cylindrical wall (also 21) having a generally constant diameter.

The diameter of the septum-receiving portion 21 is most preferably greater than the smallest pre-assembly diameter of the frustoconical portion 36 of the septum 22 but smaller than the largest pre-assembly diameter of the frustoconical portion 36 or cylindrical portion 38 of the septum 22. For example, the diameter of the septum-receiving portion 21 of the housing 16 may be approximately 0.290 inches (7.4 mm); the pre-assembly diameter of the cylindrical portion 38, which equals the largest diameter of the frustoconical portion 36, may be approximately 0.322 inches (8.2 mm); and the smallest pre-assembly diameter of the frustoconical portion 36 may be approximately 0.280 inches (7.1 mm).

The arrangement is such that the greatest compression is applied adjacent the outside end 26 of the septum 22. In the illustrative example provided above, the compression applied by the wall of the housing 16 against the cylindrical portion 38 reduces the diameter of the cylindrical portion approximately ten percent from its uncompressed configuration. FIG. 3 illustrates in phantom the configuration of the septum 22 after assembly in the housing 16.

The outer ledge 34 of the housing 16 defines a generally circular opening 40 where the outside end 26 of the septum 22 is exposed through the outside end 18 of the housing 16. The outside end 24 of the septum 22 includes an annular ridge 42 extending through the generally circular opening 40, and an annular channel 44 concentric with the annular ridge 42 and having a diameter greater than the diameter of the annular ridge 42. The outer ledge 34 has an annular inner edge 46 received in the annular channel 44 of the septum 22.

For example, the annular ridge 42 of the septum 22 may have an outer diameter of approximately 0.16 inches (4.1 mm) concentric with the central axis of the septum 22; an inner diameter of approximately 0.12 inches (3.0 mm); and a generally hemispherical cross-sectional configuration, with a cross-sectional radius of approximately 0.01 inches (0.25 mm).

The slit 30 is preferably formed in the molded septum 22 by cutting with a small blade (224 in FIG. 12), which may be inserted longitudinally through the outside surface 26 of the septum 22. As an illustrative example, if the diameter of the cannulae 12 most likely to be used in the septum 22 is approximately 0.05-0.10 inches (1.3-2.5 mm), the length of the slit 30 (laterally along the septum 22) may be approximately 0.03-0.08 inches (0.76-2.0 mm).

Most preferably, the slit-cutting blade (224 in FIG. 12) has a width of approximately 0.050 inches (1.27 mm) to cut a slit 30 having a length of approximately 0.050 inches (1.27 mm). This is believed to be optimum for use with the cannulae available under the trade designation "Needle-Less Injection Cannula", from Baxter International, Inc., Deerfield, Ill., as well as workable with the cannulae available from Abbott Laboratories, Inc., Abbott Park, Ill. under the trade designation "LifeShield Infection Control System". The outer diameter of Baxter's "Needle-Less Injection Cannula" is approximately 0.100 inches (2.5 mm), and the outer diameter of Abbott's "LifeShield" cannula is approximately 0.05 inches (1.27 mm).

Most preferably, the bore 28 of the septum 22 is larger than the diameter of the cannula 12 before the cannula 12 is introduced into the slit 30 of the septum 22. When the cannula 12 is introduced through the slit 30 (FIG. 5), the bore 28 of the septum is decreased in cross section by movement of the material of the septum 22 displaced by the cannula 12 such that the septum 22 sealingly engages the cannula 12 along the bore 28 of the septum 22.

For example, the bore 28 of the pre-assembly septum 22 preferably is generally cylindrical and has a diameter of approximately 0.120 inches (3.05 mm), which is believed to be optimum for a cannula 12 having a outside diameter of approximately 0.100 inches (2.5 mm). The diameter of the bore 28 of the septum 22 is smaller after assembly of the injection site 10 than before due to radial compression of the septum 22 in the septum-receiving portion 21 of the housing 16.

The septum 22 is preferably integrally molded of a suitable elastomeric material, such as polyisoprene (natural or synthetic). The most preferred polyisoprene materials are synthetic, and have a durometer of approximately 35 on the Shore A scale and a compression set of approximately 16.4%. Suitable polyisoprene materials include "5218 or 5251 Gum Rubber" available from Abbott Laboratories, Inc. Abbott Part, Ill.; "1028 GUM Rubber" and Catalog Nos. "2-2-3 7389-35" and "2-6-2X 7389-35" available from The West Company, Phoenixville, Penn.; and Catalog No. "L 3819" available from Neff Perkins Co., Painesville, Ohio. A silicone formulation available under Catalog No. "L 4795" from Neff Perkins Co., may also be suitable.

As used herein, "integrally molded" means molded in one continuous piece, as opposed to a number of pieces mechanically positioned together. The arrangement should be such that material displaced from the slit 30 is primarily directed to shrinking the diameter of the bore 28.

· The housing 16 is preferably injection molded of a suitable synthetic resin material, such as acrylonitrile-butadiene-styrene (ABS), or one of the copolyester or copolyester/polycarbonate blends available under the trade designations "DN003" or "DA003" from Eastman Chemical Company, Kingsport, Tenn. The material of the housing 16 is relatively un-yielding in normal use compared to the elastomeric material of the septum 22 so that the walls of the septum-receiving portion 21 of the passageway 20 do not expand significantly when the slit 30 is expanded by the cannula 12. The result is that the walls of the septum-receiving portion 21 of the passageway 20, as well as the inner and outer ledges 32 and 34, help direct the displaced material of the septum 22 to shrink the bore 28.

Most preferably, the outer ledge 34 is swaged to bend it inwardly over the outside end 26 of the septum 22 to hold the septum 22 in the housing 16 as discussed below. It is also contemplated that the outer ledge 34 could be spin swaged, ultrasonically deformed or deformed by a hot air/cold anvil process to bend it against the outside end 26 of the septum 22. Alternatively, the housing 16 could be molded in more than one piece that are assembled together to hold the septum 22 in place.

The IV injection site 10 may be in the form of a Y-site (also 10) as illustrated in the drawing, with an upstream arm 48, a downstream arm 50 and the septum-receiving portion 21. The inner walls of the upstream and downstream arms 48 and 50 define a lumen 52 extending in fluid communication with the passageway 20 along the inside end 24 of the septum 22. The upstream and downstream arms 48 and 50 are adapted to be mounted on the ends of conventional IV tubing (not shown).

The downstream arm 50 extends co-axially from the septum-receiving portion 21 so that insertion of the end 14 of the cannula 12 piercing the septum 22 is not stopped by the lumen-defining wall of the downstream arm 50. The downstream arm 50 preferably extends downwardly a distance from the outside end 26 of the septum 22 greater than the anticipated length of the cannula 12 to isolate the downstream section of IV tubing (not shown) from possible contact with the end 14 of the cannula 12.

The IV injection site 10 may be positioned along tubing sets of the types disclosed in co-assigned U.S. Pat. Nos. 4,236,880; 4,277,226; 4,322,201; 4,637,817; 4,673,390; 4,705,506; 4,714,463; and 5,017,192, which show infusion therapy systems and are incorporated herein by reference. In such a system, one injection site 10 could be positioned along the tubing set (not shown) upstream relative to an infusion pump (not shown) and another injection site 10 could be positioned along the tubing set downstream of the infusion pump.

The upstream IV injection site 10 provides a convenient mechanism to connect a second source of fluid into the multiple solution IV therapy systems disclosed in U.S. Pat. Nos. 4,637,817; 4,673,390; 4,705,506; and 4,714,463. The injection site 10 can also be used in conventional gravity flow IV tubing sets (not shown) of the type designed to be used without an infusion pump, as well as with drug vials, or other medical injection sites. As used herein "IV injection site" refers among other things to IV Y-sites; injection or withdrawal sites in drug vials holding drugs to be administered intravenously; and sampling sites through which fluid is withdrawn from a tubing set, for example, a sampling site in an extracorporeal cardiovascular support circuit.

Figure 7:
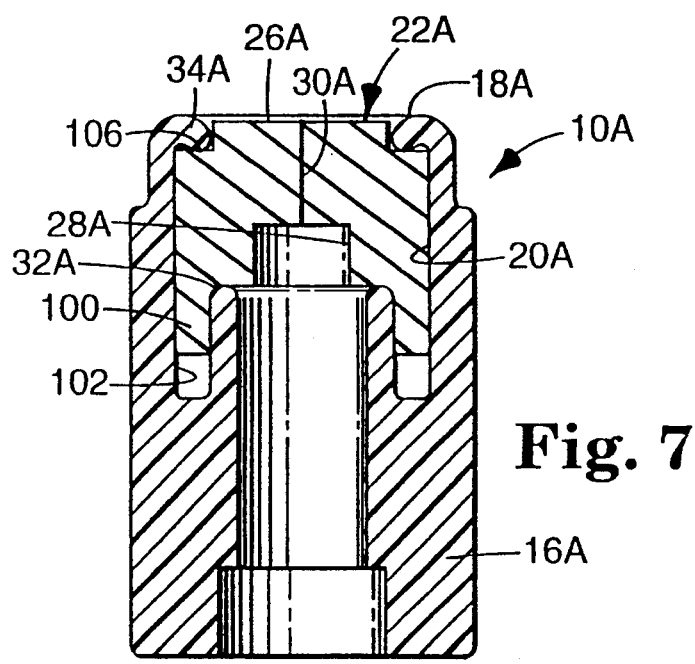
FIG. 7 is an enlarged cross-sectional view of an alternative embodiment of the IV injection site.

FIG. 7 illustrates an alternative embodiment of the IV injection site, here designated 10A, similar to injection site 10 but in which the inside end 24A of the septum 22A includes an annular skirt 100 extending longitudinally inwardly from the septum 22A. (Reference numerals ending with an "A" in FIG. 7 designate parts designated in the other figures by the same reference numerals without the "A" ending.) The inner ledge 32A of the housing 16A includes an annular skirt-receiving channel 102 for receiving the skirt 100 of the septum 22A.

The skirt 100 and skirt-receiving channel 102 help stabilize the septum 22A in the housing 16A, and the relative dimensions of the skirt 100 and channel 102 facilitate fine tuning of the change in diameter of the bore 28A when a cannula 12 is inserted into the site 10A. As illustrated in FIG. 7, the channel 102 is deeper than the skirt 10 is long, providing space for expansion of the elastomeric material of the septum 22A when a cannula 12 expands the slit 30A, with the result that the diameter of the bore 28A would not shrink as much as the bore 28 of the injection site 10. The skirt-receiving channel 102 could alternatively have a length substantially equal to the length of the skirt 100 so that more of the material displaced by the cannula 12 piercing the slit 30A is directed to shrinking the diameter of the bore 28A.

The septum 22A of the alternative injection site 10A may also include an annular stepped shoulder 104 along the periphery of its outside end 26A so that the outside end 18A of the housing 16A is approximately flush with the outside end 26A of the septum 22A. The outer ledge 34A may be ultrasonically crimped to retain the septum 22A in position. It is also contemplated that the septum 22A would be tapered (possibly similarly to the septum 22) so that the greatest radial compression is provided adjacent the outside surface 26A of the septum 22A.

Although not preferred or shown, the septum-receiving portion may alternatively have a tapered configuration, with the smallest diameter being provided adjacent the outside end of the housing, to provide greater compression along the outside surface than elsewhere along the septum, although this arrangement results in more difficult assembly of the injection site. Assembling a multi-part housing (not shown) would be one way of manufacturing a housing having such a tapered septum-receiving portion. Such a multi-part housing may include one or more parts of a different color to indicate that the injection site is intended for use with a blunt cannula.

2. Operation of Injection Site

The operation of the IV injection site 10 will now be described. First, the cannula 12 is introduced into the slit 30 of the septum 22. As this is done, the cannula 12 expands the elastomeric material of the septum 22 to enlarge the slit 30 to receive the cannula 12. Since the material of the septum 22 is practically incompressible, the elastomeric material of the septum 22 displaced by the cannula 12 is directed by the housing 16 toward the bore 28 of the septum 22 to decrease the diameter of the bore 28. The diameter of the bore 28 of the septum 22 is decreased to less than or equal to the diameter of the cannula 12.

The cannula 12 is then introduced into the bore 28 of the septum 22 by continuing to insert the cannula 12 through the slit 30. This results in the septum 22 sealingly engaging the cannula 12 along the bore 28 of the septum 22. Because the diameter of the bore 28 of the septum 22 had been decreased to less than or equal to the diameter of the cannula 12, the elastomeric material of the septum 22 along its bore 28 presses against the cannula 12 when the cannula 12 is introduced into the bore 28 of the septum 22.

When the cannula 12 is removed from the injection site 10, the septum 22 returns to its normal configuration, with the slit 30 sealing against leakage.

3. Apparatus for Making the Injection Site

Figure 12:
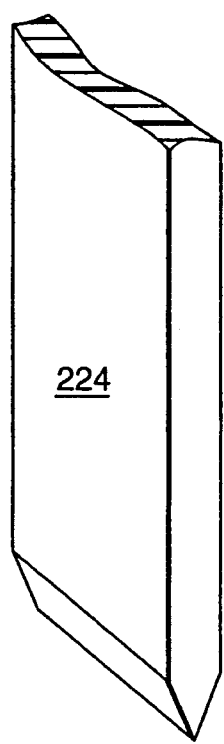
FIG. 12 is an enlarged perspective view of a knife used at the slitting station of FIGS. 8–11.
Figure 13:
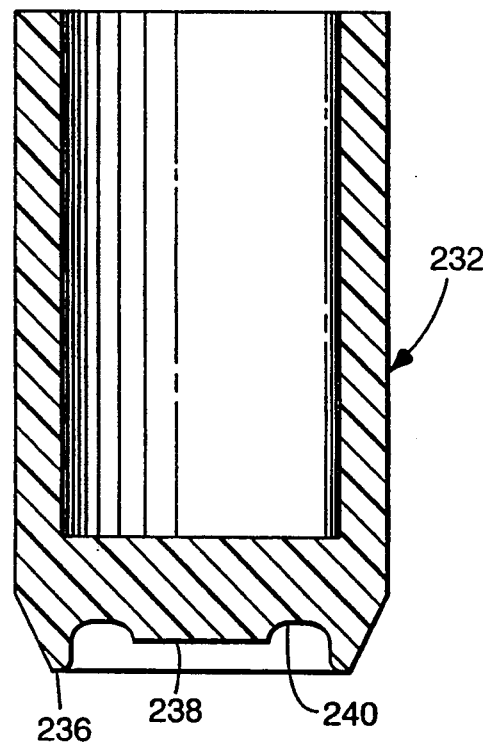
FIG. 13 is an enlarged view of a swaging tool used at the swaging station of FIGS. 8–11.
Figure 14:
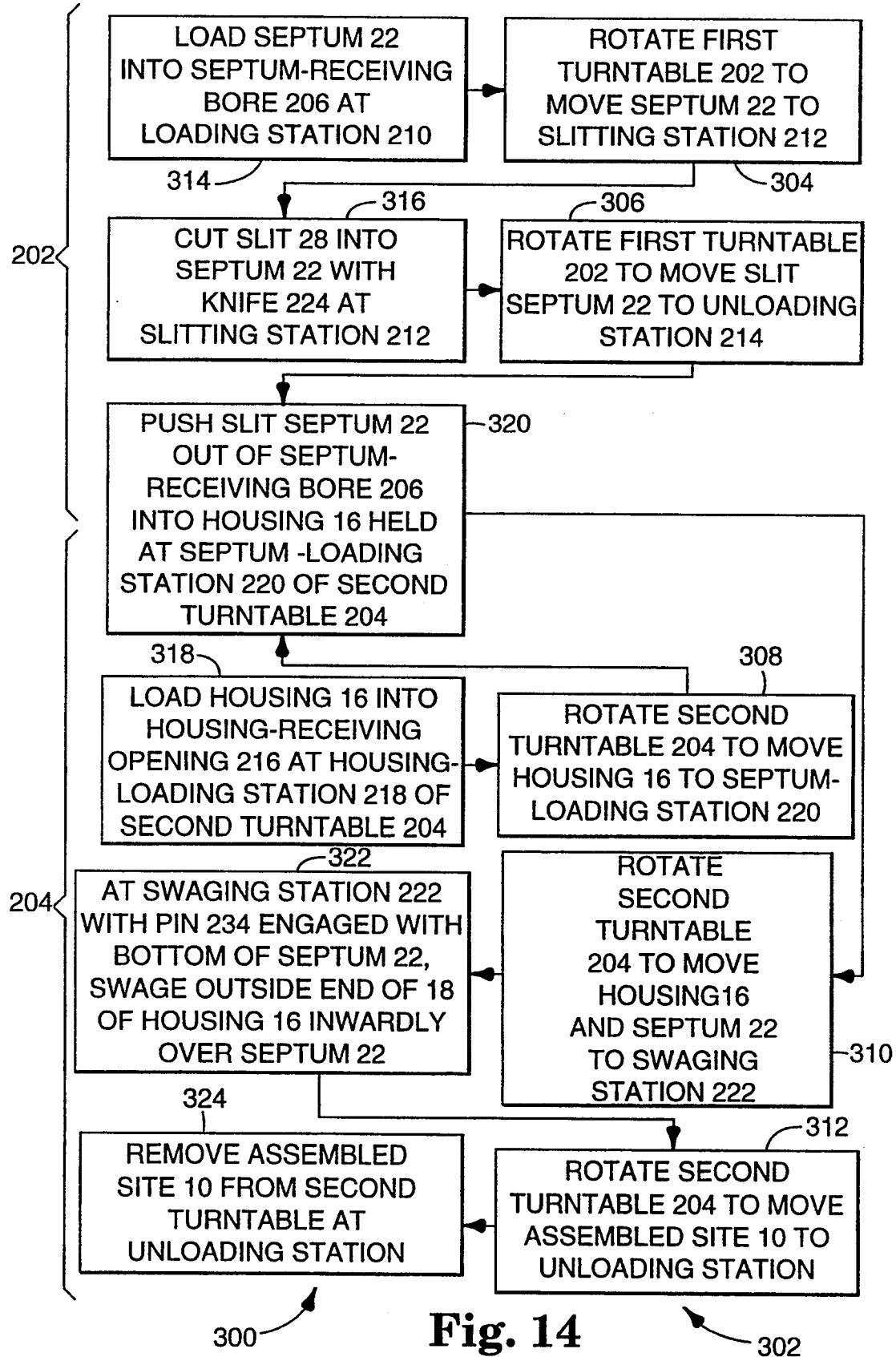
FIG. 14 is a flow chart illustrating the method of the invention of fabricating an injection or sampling site with the apparatus of FIGS. 8–13.

The apparatus 200 for making the injection or sampling site 10 will be described with reference to injection site 10 shown in FIGS. 1-6 (except that the outside end 26 of the septum 22 is flat), although the apparatus 200 may be adapted for use with other injection sites, including the injection site 10A shown in FIG. 7 and injections sites (not shown) in which the septum is not provided with a bore. FIGS. 8-13 illustrate one embodiment of the apparatus 200, and FIG. 14 is a flow chart illustrating the method of use of the apparatus 200.

Figure 10:
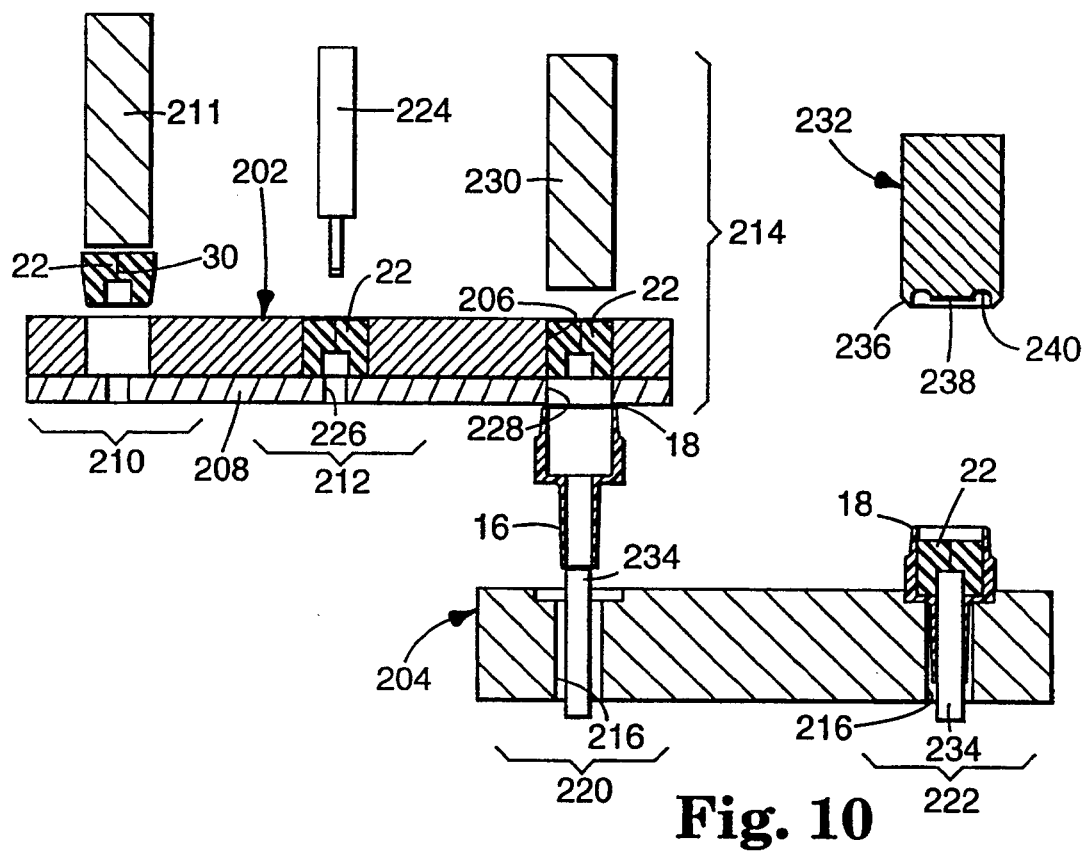
FIG. 10 is a cross-sectional view substantially along arcs of the turntables shown in FIG. 9, illustrating in a linear fashion the arrangement of selected stations relative to the first and second turntables of the apparatus.
Figure 11:
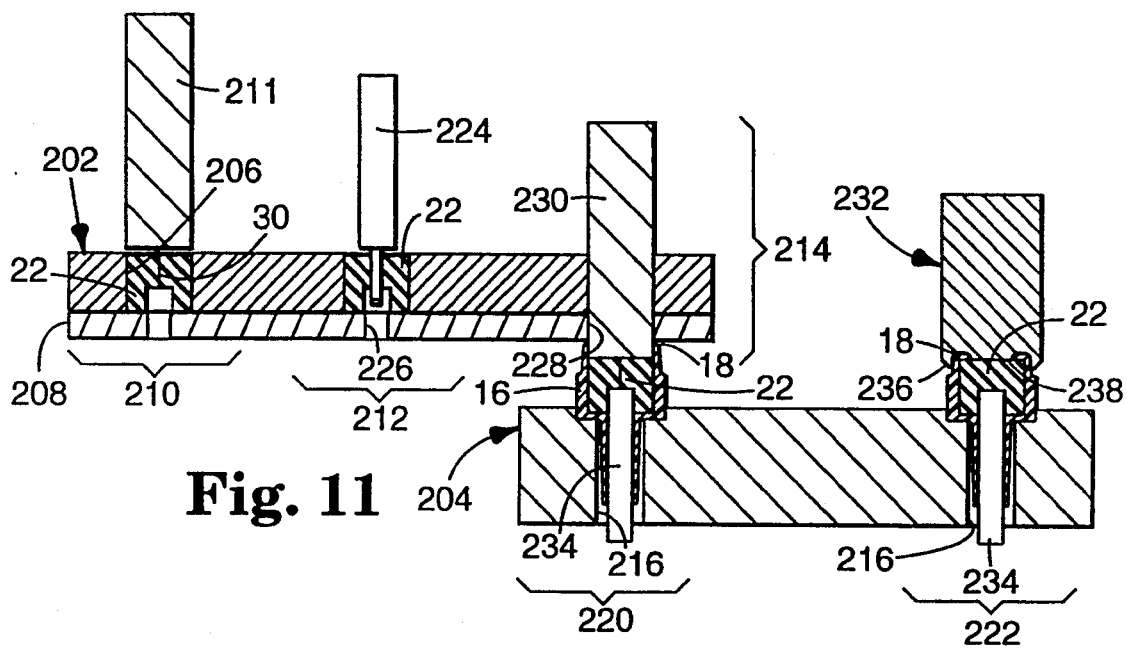
FIG. 11 is a cross-sectional view similar to FIG. 10, illustrating the substantially simultaneous cutting of a slit in the septum at the slitting site of the first turntable, transferring of the septum at the unloading station of the first turntable to the septum-loading station of the second turntable, and swaging of the housing at the swaging station of the second turntable.

As illustrated in FIGS. 8-11, apparatus 200 comprises two turntables 202 and 204. The first turntable 202 comprises a block (also 202) having a plurality of septum-receiving bores 206 for receiving the septums 22. The first turntable 202 is rotatable relative to a back support 208 between different rotational positions. At each one of these rotational positions, as illustrated in FIGS. 10 and 11, one septum-receiving bore 206 is at a loading station 210, a second septum-receiving bore 206 is at a slitting station 212 and a third septum-receiving bore 206 is at an unloading station 214.

The second turntable 204 has a plurality of housing-receiving openings 216 for receiving the housings 16. The second turntable 204 is rotatable to move the housing-receiving openings between a housing-loading station 218, a septum-loading station 220, a swaging station 222, and an unloading station 223. The unloading station 214 of the first turntable 202 and the septum-loading station 218 of the second turntable 204 are aligned to permit loading a septum 22 from the first turntable 202 into a housing 16 held in the second turntable 204.

Figure 8:
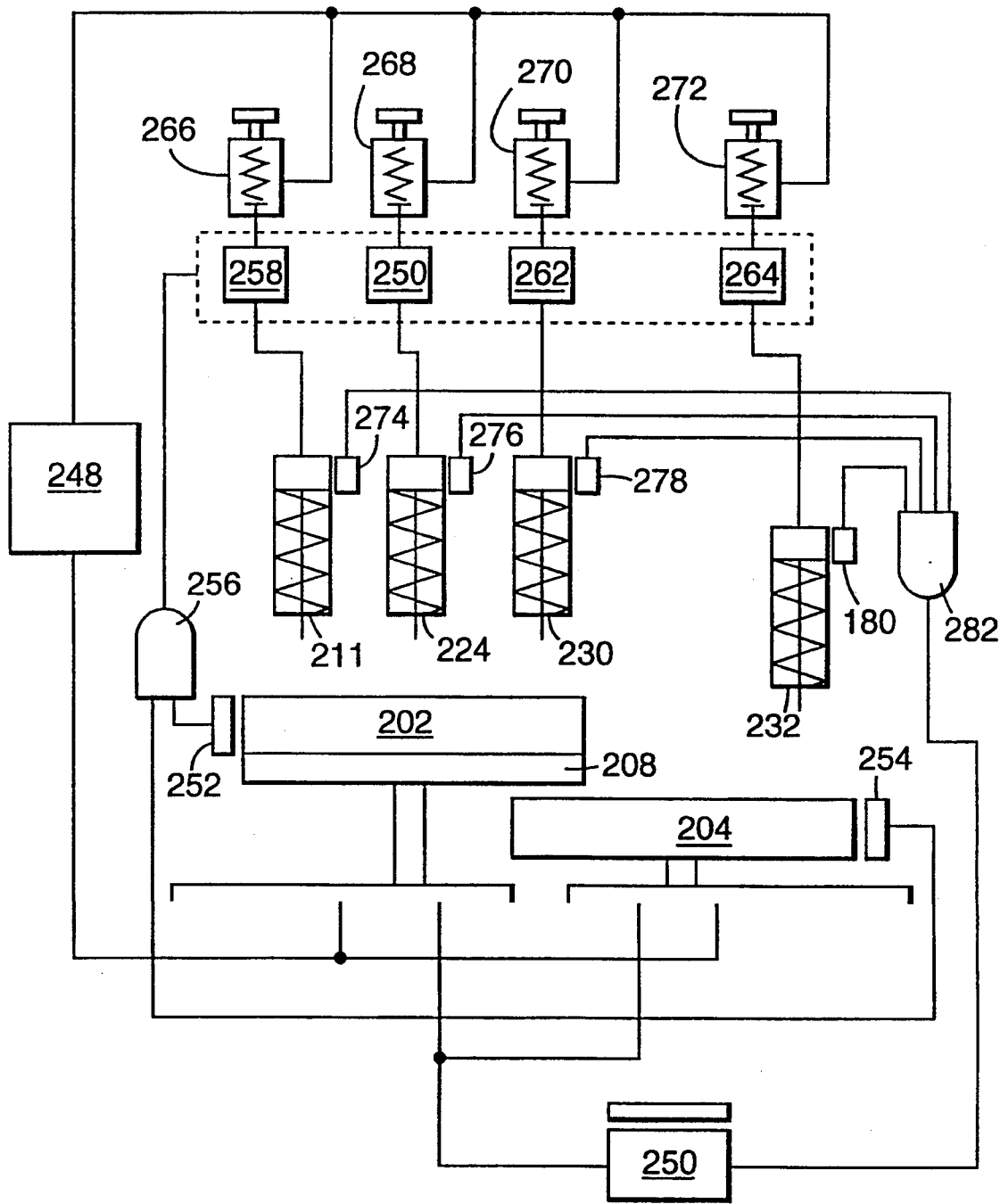
FIG. 8 is a diagrammatic view of an apparatus of the invention for fabricating injection or sampling sites.
Figure 9:
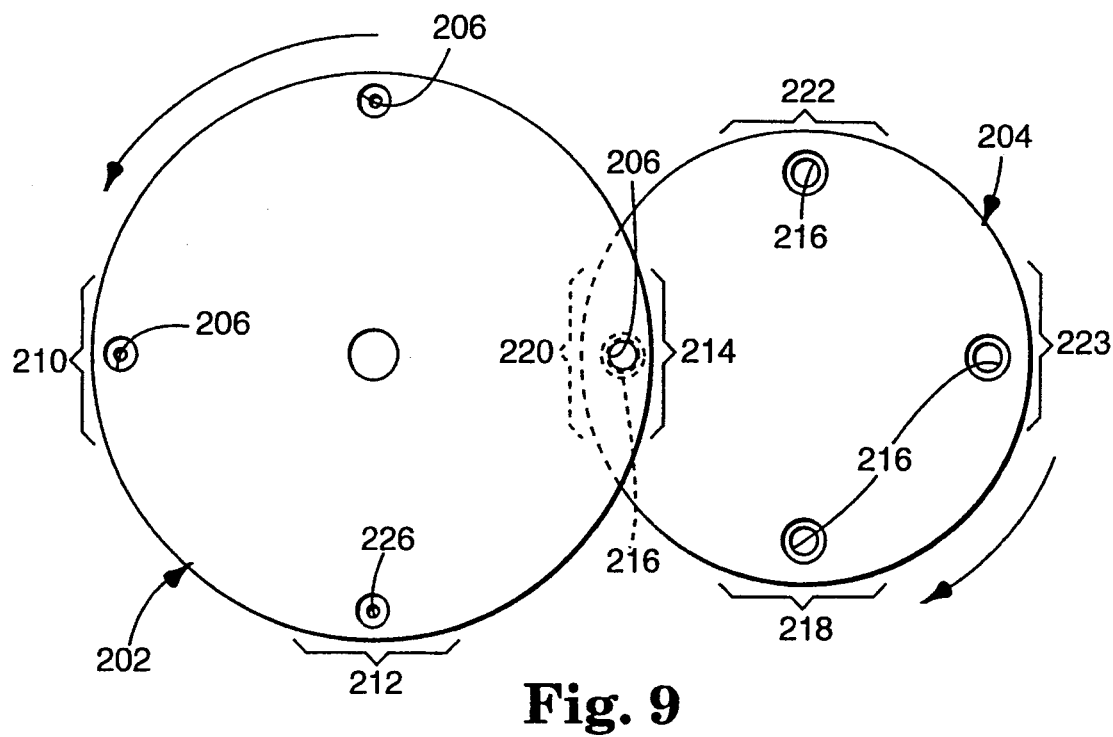
FIG. 9 is a top plan view illustrating first and second turntables of the apparatus rotatable relative to a plurality of stations, including a slitting station and a swaging station, to perform the various processes that result in an assembled injection or sampling site.

The loading station 210 of the first turntable 202 is where the septums 22 are loaded into the septum-receiving bores 206. It is contemplated that such loading may be accomplished by any suitable conventional means, including manually or automatically inserting the septums 22 into the septum-receiving bores 206. FIGS. 8, 10 and 11 show a loading means 211 for loading the septum 22 into a septum-receiving bore 206, which comprises a pusher 211 that is operable to push the septum 22 into the septum-receiving bore. The loaded septums 22 are moved to the slitting station 212 by rotation of the first turntable 202.

The first turntable 202 is part of the slit cutting means of the apparatus 200, which includes at the slitting station 212 a knife 224 that is movable relative to the septum-receiving bore 206 positioned at the slitting station 212 to cut a slit 30 into the septum 22 received in that septum-receiving bore 206. A preferred configuration of the knife 224 has a sharp, chisel-shaped edge as illustrated in FIG. 12. The back support 208 preferably has a knife-receiving opening 226 in alignment with the knife 224 for receiving the knife 224 when the slit 30 is cut into the septum 22.

At the slitting station 212, the back support 208 supports the septum 22 to hold the septum 22 in the septum-receiving bore 206 while the knife 224 is cutting the slit 28 into the septum 22. When at the slitting station 212, a septum-receiving bore 206 of the first turntable 202 is not adjacent the passageway 228 through the back support 208.

The septum-receiving bores 206 laterally or radially capture and constrain the septums 22 to prevent lateral or radial movement of the septums 22 while the knife 224 is cutting the slit 30. This is believed to result in consistently aligned or centered slits 30 in the septums 22.

The septum-receiving bores 206 are preferably generally cylindrical having a generally constant diameter substantially equal to the diameter of the septum-receiving portion 21 of the passageway 20 of the housing 16 into which the septum 22 will be inserted. This diameter provides substantially equal radial compression to the septum 22 as it will have when inserted into the housing 16, which is helpful in maintaining proper alignment of the slit 30 relative to the housing 16. As an alternative, the septum-receiving bores (not shown) may have a frustoconical configuration generally corresponding to the frustoconical configuration of the preferred septum 22, or the septum-receiving bores (also not shown) may have other configurations generally corresponding to the septum-receiving portion of the particular housing being used.

The first turntable 202 is designed to rotate the septum-receiving bore 206 that is at the slitting station 212 to the unloading station 214 after the septum 22 in that septum-receiving bore 206 has been slitted. At the unloading station 214, the back support 208 is provided with a passageway 228 to allow the septum 22 to be pushed through the passageway 228 with a suitable pushing means, such as a push rod or tool 230, to remove the septum 22 from the septum-receiving bore 206 and insert the septum 22 into the passageway 20 of a housing 16 held at the septum-loading station 220 of the second turntable 204. Preferably, the passageway 228 at the unloading station 214 is at least equal in cross sectional size to a septum-receiving bore 206, but the passageway 228 may be sized substantially larger than the size of the septum-receiving bore 206.

The second turntable 204 is a part of the apparatus 200 designed to hold housings 16 (a) to load a septum 22 into each housing 16, and (b) to swage the outside end 18 of the housing 16 inwardly over the septum 22 loaded therein. The slitting part (e.g., stations 210, 212 and 214) of the apparatus 200 could be used separately, or in a different process, such as one where a cap (not shown) is mounted on the housing to hold the septum in position, or with a different type of second turntable than will be described herein. The swaging part (e.g., stations 218, 220 and 222) of the apparatus 200 could be used separately from the slitting part, or could be used with a different slitting process, for example, a process in which the slit is cut into a septum that has already been loaded into the housing, before or after swaging the housing.

The housing-loading station 218 of the second turntable 204 is where the housings 16 are loaded into the housing-receiving openings 216. It is contemplated that such loading may be accomplished by any suitable means, including manually or automatically inserting the housings 16 into the housing-receiving openings 216. For example, a conventional hopper or shaker table (not shown) may be used to provide housings 16 to the housing-receiving openings 216. The housing-receiving openings 216 may have a configuration permitting only up-right placement of the housings 16, with their outside ends 18 facing upwardly.

The loaded housings 16 are moved from the housing-loading station 218 to the septum-loading station 220 by rotation of the second turntable 204. At the septum-loading station 220, a housing-receiving opening 216 is aligned with the passageway 228 of the back support 208, and with the septum-receiving bore 206 of the first turntable 202 that is at the unloading station 214, to enable the septum 22 held in that septum-receiving bore 206 to be loaded in the housing 16 held at the septum-loading station 220. As discussed above with respect to the first turntable 202, the septums 22 are pushed from the unloading station 214 of the first turntable 202 into the housing 16 held at the septum-loading station 220 of the second turntable 204 by the pushing tool 230. The septum 22 and housing 16 are then moved from the septum-loading station 220 to the swaging station 222 by rotation of the second turntable 204.

The swaging station 222 includes a swaging tool 232 for swaging the outside end 18 of the housing 16 inwardly over the septum 22 (see, e.g., FIG. 11), and a pin 234 that is inserted into the lower end of the passageway 20 of the housing 16 against the lower part of the septum 22 to prevent movement of the septum 22 into the passageway 20 of the housing 16 during the swaging operation. When used with septums 22 having a bore 28 therein, the pin 234 is configured to be closely received in the bore 28 of the septum 22 to prevent movement of the material of the septum 22 into the bore 28.

At the swaging station 222, a housing-receiving opening 216 is aligned with the swaging tool 232 to enable the swaging tool 232 to swage the outside end 18 of a housing 16 received in that housing-receiving opening 216. The pin 234 is in alignment with that housing-receiving opening 216, the passageway 20 of the housing held in that housing-receiving opening 216, and the swaging tool 232.

The preferred arrangement of the swaging tool 232 and pin 234 is such as to substantially completely constrain the septum 22 in position in the septum-receiving portion 21 of the housing 16. As best illustrated in FIG. 13, the end 236 of the swaging tool 232 is preferably configured to include a septum-engaging portion 238 that engages the outside end 26 of the septum 24 to prevent additional downward movement of the swaging tool 232 when the outside end 18 of the housing 16 just touches the outside end 26 of the septum 22.

Because (a) the elastomeric material of the septum 22 is volumetrically incompressible; and (b) movement and deformation of the septum 22 are prevented by the pin 234, the passageway-defining walls of the housing 16 and septum-engaging portion 238 of the swaging tool 232; the outer ledge 34 formed by the swaged outside end 18 of the housing 16 is prevented from longitudinally compressing the septum 22. This is believed to improve the consistency of the septums 22 assembled in injection sites 10 with this apparatus 200 compared with conventional swaging apparatus so that the insertion force required to insert a blunt cannula 12 through the slit 30 of the septum 22 is consistent, notwithstanding variations in the septums 22 and housings 16 fed into the apparatus 200.

In conventional swaging processes, normal tolerances for septums, which are molded of elastomeric materials (e.g., latex rubber), can provide significant performance differences when held in swaged housings due to inconsistent vertical or longitudinal compression of the septums. For example, if three varying thickness septums are placed in a housing, and the outside end of the housing is swaged over the septum by conventional swaging apparatus (not shown): (a) the relatively thick septum may be overly compressed increasing the required penetration force that must be exerted to insert a cannula through the septum, (b) in extreme cases there may actually be a gap between the relatively thin septum and the swaged end of the housing, and (c) only the septum having the normal thickness will provide the specified penetration force required to penetrate the septum with a blunt cannula. "Conventional swaging apparatus" refers to apparatus that does not include a pin 234 and does not include a septum-engaging portion 238 on the swaging tool 232.

On the other hand, with the apparatus 200 of this invention, if the thickness of one septum 22 is slightly greater than another septum 22, the swaging station 222 is designed to bring the outer ledge 34 into contact with either septum 22 without a gap (or at most with a minimal gap) in the case of the thinner septum 22 and without vertical or longitudinal compression of the relatively thicker septum 22. The penetration force required to insert a blunt cannula 12 through any one of the septums 22 (e.g., thick, thin, exactly as specified) will be consistent.

Most preferably, the septum-engaging portion 238 of the swaging tool 232 projects downwardly from the housing-engaging portion 240 of the tool 232 a distance substantially equal to, or slightly greater than, the wall thickness of the outside end 18 of the housing 16 being swaged. For example, if swaging the outside end 18 of a housing 16 having a wall thickness of approximately 0.025 inches (0.635 mm), the septum-engaging portion 238 may project approximately 0.025 inches (0.635 mm) beyond the housing-engaging portion 240. The housing-engaging portion 240 most preferably defines a annular groove (also 240) having rounded surfaces to facilitate bending the housing wall inwardly over the septum 22. It will be observed that the foregoing arrangement of the swaging tool 232 and pin 234 enables swaging the housing 16 without deforming the septum 22 in the longitudinal direction (vertically in the drawings).

Also, preferably, the swaging tool 232 is driven by any suitable means 242, such as pneumatic means as illustrated in FIG. 8, that applies a limited, predetermined amount of force to the septum 22 at which point the swaging process is complete. Since the septum 22 is incompressible and constrained from escape by the housing 16, pin 234 and septum-engaging portion 238 of the swaging tool 232, the force generated by the swaging tool 232 should be limited to prevent breakage of the apparatus 200 or housing 16.

Indexing means may be provided facilitate stopping each septum-receiving bore 206 of the first turntable 202 and housing-receiving opening 216 of the second turntable 204 at the next station of the apparatus 200. The indexing means may comprise any suitable manually operable means (not shown) including a detent mechanism, such as a plurality of detent cavities (not shown) arranged around the first and second turntables 202 and 204 that receive at the proper aligned positions a spring-loaded ball (not shown). The manually operable means could comprise a mechanical linkage between the two turntables, a drive mechanism, and a ratchet mechanism to ensure completion of the slitting, pushing and swaging operations before the turntables are advanced. A lever (not shown) could be included for manual operation of the drive mechanism.

Most preferably, automatic or semi-automatic means are provided for advancing the turntables 202 and 204; driving the pusher 211, knife 224, pushing tool 230 and swaging tool 232; and indexing the turntables 202 and 204 for proper alignment relative to the various stations. For example, a preferred semi-automatic means is illustrated in FIG. 8.

Conventional turntable drive mechanisms 244 and 246 are provided to advance the turntables 202 and 204 from station to station, with the drive mechanisms 244 and 246 providing an indexing function to stop the turntables 202 and 204 in proper alignment with the stations. The drive mechanisms 244 and 246 are driven by compressed air from a source 248 of compressed air, with the drive mechanisms 244 and 246 being provided with internal pressure regulators (not shown). Rotary indexing tables having pneumatic drive mechanisms are commercially available from Air-Hydraulics, Inc., Jackson, Mich.

A manually operable button 250 is provided for starting the drive mechanisms 244 and 246. The preferred button 250 includes an electronically-activated reset mechanism to prevent restarting the drive mechanisms 244 and 246 until after a signal has been provided indicating that the pushing, slitting and swaging operations have been completed. In the semi-automatic version, an operator would manually load a septum 22 into the first turntable 202 at the loading station 210 and a housing 16 into the second turntable 204 at the housing-loading station 218 before pushing the button 250. Sensing means (not shown) may also be provided to prevent operation of the button 250 until after a septum 22 and housing 16 have been loaded.

Sensors 252 and 254 are provided to sense the position of the turntables 202 and 204 to indicate whether they have moved to the proper positions, with the septums 22 and housings 16 advanced to their next stations. Each sensor 252 and 254 provides a signal to an AND gate 256, with the AND gate 256 providing a signal to activate conventional pneumatic valves 258, 260, 262 and 264 after both turntables 202 and 204 have rotated to their next stations.

The pneumatic valves 258, 260, 262 and 264 permit compressed air communication with the pusher mechanism 211, knife mechanism 224, pushing tool 230 and swaging tool 232 to substantially simultaneously (a) push a septum 22 into a septum-receiving bore 206 at the loading station 210; (b) cut a slit into a septum 22 at the slitting station 212; (c) transfer a slit septum 22 from the unloading station 214 of the first turntable 202 into a housing 16 at the septum-loading station 220 of the second turntable 204; and (d) swage the outside end 18 of the housing 16 inwardly over the septum 22 at the swaging station 222.

Each valve 258, 260, 262 and 264 is maintained in compressed air communication with the source 248 of compressed air via its respective conventional pressure regulator 266, 268, 270 and 272. Most preferably, each pressure regulator 266, 268, 270 and 272 is individually set or adjusted to provide an individually appropriate air pressure to operate each of the pusher 211, knife 224, pushing tool 230 and swaging tool 232. It is also contemplated that the septum-engaging pin 234 could be pneumatically driven in the manner illustrated with respect to the swaging tool 232 and other pneumatically driven tools.

Sensing means 274, 276, 278 and 280 are preferably provided for respectively sensing the position of the pusher 211, knife 224, pushing tool 230 and swaging tool 232 to determine whether they have (a) moved so as to perform their respective functions (FIG. 11), and (b) returned to their retracted positions (FIG. 10) to allow the turntables 202 and 204 to rotate to their next stations. The sensing means 274, 276, 278 and 280 may take any suitable form, including a combination of Hall effect sensors, force indicators and logic circuitry designed to determine whether the respective tools have performed their functions and returned. For example, one conventional Hall effect sensor may be positioned to sense whether a specific tool (e.g., the swaging tool 232) has reached its extreme operational position (e.g., the position where swaging is completed which is illustrated in FIG. 11), and another conventional Hall effect sensor may be positioned to sense whether that tool has returned to its retracted position (FIG. 10).

Each one of the sensing means 274, 276, 278 and 280 provides a signal to an AND gate 282, which in turn provides a signal to the button 250 to reset the button 250. The arrangement is such that the button 250 is not reset (and thus not enabled to trigger rotation of the turntables 202 and 204) until after the sensing means 274, 276, 278 and 280 have signaled that each of the pusher 211, knife 224, pushing tool 230 and swaging tool 232 have performed their functions and returned to their retracted positions (FIG. 10). As an alternative, the AND gate 282 can provide its signal directly to the turntable drive mechanisms 244 and 246 to automatically advance them without requiring manually operating a button.

4. Method of Making the Injection Site

The method of making the injection or sampling site 10 is illustrated in FIG. 14. As illustrated in the flow chart, the steps of the method are divided into two columns 300 and 302. The first column 300 shows the "operational" steps performed on the septum 22 and/or housing 16, which are preferably performed substantially simultaneously. As used herein, the term "operational steps" merely refer to something being performed on the septums 22 or housings 16 other than rotation of the turntables 202 and 204 to advance the septums 22 or housings 16 to their next stations.

The second column 302 shows the transfer steps 304, 306, 308, 310 and 312 during which the septums 22 and/or housings 16 are advanced to the next stations 210, 212, 214, 218, 220, 222 and 223. The transfer steps 304, 306, 308, 310 and 312 most preferably comprise merely rotating the turntables 202 and 204 to advance the septums 22 and housings 16 to their next stations. All of these transfer steps 304, 306, 308, 310 and 312 are performed substantially simultaneously.

The flow chart is also divided into an upper portion designated 202 to indicate that the steps performed in the upper portion of the flow chart are most preferably performed on the first turntable 202, and a lower portion designated 204 to indicate that the steps performed in the lower portion of the flow chart are most preferably performed on the second turntable 204.

The first operational step 314 is to insert an un-slit septum 22 into a septum-receiving bore 206 at the loading stations 210 of the first turntable 202. For example, this may be performed by pushing the septum 22 into the septum-receiving bore 206 with the pneumatically operated pusher 211. The un-slit septum 22 is then advanced to the slitting station 212 in the transfer step 304 by rotating the first turntable 202. It will be observed that the sensing means 274 prevents advancing the septum 22 to the slitting station 212 until after the first operational step 314 is completed and the pusher 211 returned to its retracted position (FIG. 10).

The second operational step 316 is to cut a slit into the septum 22 with the knife 224 by pushing the knife 224 longitudinally into the septum 22 (FIG. 11). The knife 224 may actually be pushed through the septum 22 into the knife-receiving opening 226 in the back support 208. After the knife 224 is retracted, the slit septum 22 is advanced to the unloading station 214 in the transfer step 306 by rotating the first turntable 202. Sensing means 276 prevents advancing the septum 22 to the unloading station 214 until after the knife 224 has cut the slit 30 and been moved to its retracted position. Most preferably, the sensing means includes both Hall effect positional sensors, as described above and a force sensor or switch to indicate the force applied by the knife 224 to the septum 22 to determine whether the knife 224 is broken or not to ensure that a slit 30 is made in each septum 22.

Preferably, at the same time as the first operational step 314 (loading the septum 22 into the first turntable 202) is being performed, the third operational step 318 is performed. The third operational step is to insert a housing 16 into the housing-receiving opening 216 at the housing-loading station 218 of the second turntable 204. The housing 16 may be loaded either manually or automatically, e.g., via a hopper or conveyer means (not shown). After the housing 16 is loaded into the second turntable 204 at the housing-loading station 218, the housing 16 is advanced to the septum-loading station 220 in the transfer step 308 by rotating the second turntable 204. At the septum-loading station 220, the septum-receiving portion 21 of the passageway 20 of the housing 16 is aligned with the septum-receiving bore 206 and the passageway 226 of the back support 208 that are at their unloading station 214. Most preferably, a sensor (not shown) is provided that prevents advancing the turntable 204 if a housing 16 has not been loaded into the housing-receiving opening 216.

The fourth operational step 320 is to push (with the pushing tool 230) the slit septum 22 out of the septum-receiving opening 206 at the unloading station 214 of the first turntable 202, through the passageway 228 of the back support 208, and into the septum-receiving portion 21 of the housing 16 held at the septum-loading station 220 of the second turntable 204. After the slit septum 22 has been loaded into the housing 16 at the septum-loading station, the housing 16 and septum 22 are advanced to the swaging station 22 in the transfer step 310 by rotating the second turntable 204. The sensing means 262 prevents advancing the turntable 204 until after the septum 22 has been inserted into the housing 16 with the pushing tool 230 and the pushing tool 230 has been moved to its retracted position.

The fifth operational step 322 can be subdivided into two steps: (a) before swaging the housing 16, inserting a pin 234 into the passageway 20 of the housing 16 into engagement with the inside end 24 of the septum 22, and in particular into the bore 28 of the septum; and then (b) swaging the outside end 18 of the housing 16 held at the swaging station 222 inwardly over the septum 22.

The step of inserting the pin 234 can be performed simultaneously with the step of swaging the outside end 18 of the housing 16, or it can be performed before the swaging process is started. For example, the pin 234 could be fixed in the housing-receiving opening 216 of the second turntable 204 so that it engages the inside end 24 and bore 30 of the septum 22 when the septum 22 is loaded into the housing 16 at the septum-loading station 220.

The pin 234 engages the inside end 24 of the septum 22 and fills the bore 28, if any, of the septum 22 to reduce or prevent expansion of the septum 22 inwardly through the passageway 20 of the housing 16 when the outside end 18 of the housing 16 is swaged. The swaging tool 232 includes a septum-engaging portion 238 which is configured to engage the outside end 26 of the septum 22 to prevent expansion of the septum 22 outwardly. The annular groove 240 constitutes the housing-engaging portion 240 of the swaging tool 232 which is the part of the tool 232 that is actually swaging the outside end 18 of the housing 16.

The swaging tool 232 stops trying to swage the housing 16 when the tool 232 applies a predetermined amount of force to the septum 22. For example, the pressure regulator 272 may be set to regulate this force, or a spring (not shown) may be provide in the swaging tool 232.

After the swaging process is completed, the assembled injection site 10 is advanced to the unloading station 223 in transfer step 312 by rotating the second turntable 204. The sensing means 272 prevents advancing the second turntable 204 until after the swaging process is completed and the swaging tool 232 moved to its retracted position. The sixth operational step 324 is to remove the assembled injection or sampling site 10 from the second turntable 204 at the unloading station 223. For example, the site 10 can be ejected from the turntable 204 by a blast of compressed air from the source 248 of compressed air.

It will be observed that various operations may be performed on the different septums 22 and housings 16 at the same time. For example, the outside end 18 of one housing 16 is swaged at the swaging station 222 at the same time that a slit 30 is cut into a septum 22 at the slitting station 212.

On one level, the method includes two general steps 300 and 302: (a) performing various operations on the septums and housings 16 (e.g., operational steps 314, 316, 318, 320, 322 and 324); and (b) transferring the septums 22 and housings 16 to their next stations (e.g., transfer steps 304, 306, 308, 310 and 312). These two general steps 300 and 302 are performed in alternating fashion.

As various changes could be made in the above constructions and methods without departing from the scope of the invention, it is intended that all matter contained in the above description or shown in the accompanying drawing be interpreted as illustrative and not in a limiting sense.

We claim:

1. A method of fabricating an injection or sampling site adapted to receive a blunt cannula, the method comprising the steps of:
   providing a housing having an outside end and a passageway extending inwardly from the outside end, the passageway opening through the outside end and defining a longitudinal direction;
   providing an elastomeric septum having an outside end corresponding to the outside end of the housing and an inside end opposite its outside end;
   inserting the elastomeric septum into the passageway of the housing;
   inserting a pin into the passageway of the housing to engage the inside end of the septum to reduce or prevent expansion of the septum inwardly through the passageway when the outer end of the housing is swaged; and
   during or after the step of inserting the pin, swaging the outside end of the housing inwardly over the septum with a swaging tool.

2. A method according to claim 1 further comprising:
   during the step of swaging the outside end of the housing inwardly over the septum with a swaging tool, directly engaging the septum with a septum-engaging portion of the swaging tool; and
   stopping the swaging process when the swaging tool applies a predetermined amount of force to the septum.

3. A method according to claim 2 wherein the septum has a bore extending part-way through the septum from the inside end of the septum; the step of inserting a pin into the passageway of the housing including inserting the pin into the bore of the septum.

4. A method according to claim 3 wherein the swaging tool has a septum-engaging portion and a housing-swaging portion, the step of stopping the swaging process further comprising engaging the septum with the septum-engaging portion of the swaging tool before stopping the swaging process.

5. A method according to claim 2 wherein the step of providing an elastomeric septum includes the step of cutting a slit into the septum before the septum is inserted into the passageway of the housing.

6. A method according to claim 5 wherein the step of cutting a slit into the septum comprises:
   providing an apparatus for slitting the septum comprising a block having a septum-receiving bore, a back support for supporting one end of the septum, and a knife;
   inserting the septum into the septum-receiving bore against the back support, with the septum-receiving bore laterally constraining the septum to prevent lateral deformation of the septum;
   cutting the slit into the septum with the knife axially aligned with the septum-receiving bore; and
   removing the septum from the septum-receiving bore.

7. A method according to claim 6 wherein the back support has a passageway sized to allow the septum to be pushed through the passageway of the back support, the block being movable relative to the back support between a slitting station, in which the passageway of the back support is not adjacent the septum-receiving bore of the block, and an unloading station, in which the septum-receiving bore of the block is aligned with the passageway of the back support, the apparatus further comprising a pushing tool for pushing the septum out of the septum-receiving bore and through the passageway of the back support;
   the step of removing the septum from the septum-receiving bore comprising:
   moving the block relative to the back support to the unloading station; and
   pushing the septum out of the septum-receiving bore and through the passageway of the back support with the pushing tool.

8. A method according to claim 7 wherein the step of inserting the septum into the septum-receiving bore against the back support includes inserting the septum into the septum-receiving bore such that the inside end of the septum engages the back support;
   the step of inserting the elastomeric septum into the passageway of the housing comprising:
   aligning the passageway of the housing with the septum-receiving bore of the block and passageway of the back support at the unloading station; and
   after the step of pushing the septum out of the septum-receiving bore, continuing to push the septum with the pushing tool into the passageway of the housing.

9. A method according to claim 6 wherein the back support has a knife-receiving opening, the step of cutting the slit into the septum comprising pushing the knife into the septum toward the knife-receiving opening.

10. A method according to claim 2 wherein the swaging tool has a septum-engaging portion and a housing-swaging portion, the step of stopping the swaging process further comprising engaging the septum with the septum-engaging portion of the swaging tool before stopping the swaging process.

11. A method according to claim 10 wherein the septum-engaging portion and housing-swaging portion of the swaging tool are configured such that the septum-engaging portion of the swaging tool applies the predetermined force to the septum without the swaged outside end of the housing applying longitudinal compression to the septum; the step of stopping the swaging process comprising:

stopping the swaging process before the swaged outside end of the housing applies longitudinal compression to the septum.

12. A method according to claim 2 wherein the housing has an inner ledge defining the inner end of a septum-receiving portion of the passageway; the step of inserting the septum into the passageway comprising inserting the septum into the passageway such that the inside end of the septum engages the inner ledge.

13. A method according to claim 12 wherein the septum has a bore extending part-way through the septum from the inside end of the septum; the step of inserting a pin into the passageway of the housing including inserting the pin into the bore of the septum.

14. A method according to claim 13 wherein the swaging tool has a septum-engaging portion and a housing-swaging portion, the step of stopping the swaging process further comprising engaging the septum with the septum-engaging portion of the swaging tool before stopping the swaging process.

15. A method according to claim 12 wherein the swaging tool has a septum-engaging portion and a housing-swaging portion, the step of stopping the swaging process further comprising engaging the septum with the septum-engaging portion of the swaging tool before stopping the swaging process.

16. A method according to claim 15 wherein the septum-engaging portion and housing-swaging portion of the swaging tool are configured such that the septum-engaging portion of the swaging tool applies the predetermined force to the septum without the swaged outside end of the housing applying longitudinal compression to the septum; the step of stopping the swaging process comprising:

stopping the swaging process before the swaged outside end of the housing applies longitudinal compression to the septum, the swaged outside end of the housing defining an outer ledge defining the outer end of the septum-receiving portion of the passageway.

17. A method according to claim 1 wherein the septum has a bore extending part-way through the septum from the inside end of the septum; the step of inserting a pin into the passageway of the housing including inserting the pin into the bore of the septum.

18. A method according to claim 1 wherein the step of providing an elastomeric septum includes the step of cutting a slit into the septum before the septum is inserted into the passageway of the housing.

19. A method according to claim 18 wherein the step of cutting a slit into the septum comprises:

providing an apparatus for slitting the septum comprising a block having a septum-receiving bore, a back support for supporting one end of the septum, and a knife;

inserting the septum into the septum-receiving bore against the back support, with the septum-receiving bore laterally constraining the septum to prevent lateral deformation of the septum;

cutting the slit into the septum with the knife axially aligned with the septum-receiving bore; and removing the septum from the septum-receiving bore.

20. A method according to claim 19 wherein the back support has a passageway sized to allow the septum to be pushed through the passageway of the back support, the block being movable relative to the back support between a slitting station, in which the passageway of the back support is not adjacent the septum-receiving bore of the block, and an unloading station, in which the septum-receiving bore of the block is aligned with the passageway of the back support, the apparatus further comprising a pushing tool for pushing the septum out of the septum-receiving bore and through the passageway of the back support;

the step of removing the septum from the septum-receiving bore comprising:

moving the block relative to the back support to the unloading station; and pushing the septum out of the septum-receiving bore and through the passageway of the back support with the pushing tool.

21. A method according to claim 20 wherein the step of inserting the septum into the septum-receiving bore against the back support includes inserting the septum into the septum-receiving bore such that the inside end of the septum engages the back support;

the step of inserting the elastomeric septum into the passageway of the housing comprising:

aligning the passageway of the housing with the septum-receiving bore of the block and passageway of the back support at the unloading station; and after the step of pushing the septum out of the septum-receiving bore, continuing to push the septum with the pushing tool into the passageway of the housing.

22. A method according to claim 19 wherein the back support has a knife-receiving opening, the step of cutting the slit into the septum comprising pushing the knife into the septum toward the knife-receiving opening.

23. A method according to claim 1 wherein the housing has an inner ledge defining the inner end of a septum-receiving portion of the passageway; the step of inserting the septum into the passageway comprising inserting the septum into the passageway such that the inside end of the septum engages the inner ledge.

24. A method according to claim 23 wherein the septum has a bore extending part-way through the septum from the inside end of the septum; the step of inserting a pin into the passageway of the housing including inserting the pin into the bore of the septum.

25. A method of fabricating an injection or sampling site adapted to receive a blunt cannula, the method comprising the steps of:

providing a housing having an outside end and a passageway extending inwardly from the outside end, the passageway opening through the outside end and defining a longitudinal direction;

inserting an elastomeric septum into the passageway of the housing;

swaging the outside end of the housing inwardly over the septum with a swaging tool, the swaging tool having a septum-engaging portion configured for directly engaging the septum before the swaged outside end of the housing applies longitudinal compression to the septum;

during the step of swaging the outside end of the housing inwardly over the septum with a swaging tool, directly engaging the septum with the septum-engaging portion of the swaging tool; and during he step of directly engaging the septum with the septum-engaging portion of the swain tool and before the swaged outside end of the housing applies longitudinal compression to the septum, stopping the swaging process when the swaging tool applies a predetermined amount of force to the septum at the location where the septum-engaging portion of the swaging tool is engaging the septum.

26. A method according to claim 25 further comprising the step of cutting a slit into the septum before the septum is inserted into the passageway of the housing.

27. A method according to claim 25 wherein the housing has an inner ledge defining the inner end of a septum-receiving portion of the passageway; the step of inserting the septum into the passageway comprising inserting the septum into the passageway such that the inside end of the septum engages the inner ledge.

28. A method of fabricating an injection or sampling site adapted to receive a blunt cannula, the method comprising the steps of:

providing a housing having an outside end and a passageway extending inwardly from the outside end, the passageway opening through the outside end and defining a longitudinal direction;

inserting an elastomeric septum into the passageway of the housing, the septum having an outside end corresponding to the outside end of the housing, and an inside end opposite the outside end of the septum;

swaging the outside end of the housing inwardly over the septum with a swaging tool, the swaging tool having a septum-engaging portion configured for directly engaging the septum before the swaged outside end of the housing applies longitudinal compression to the septum;

before or during the step of swaging the outer end of the housing, inserting a pin into the passageway of the housing to engage the inside end of the septum to reduce or prevent expansion of the septum inwardly through the passageway when the outer end of the housing is swaged; and stopping the swaging process when the swaging tool applies a predetermined amount of force to the septum at the location where the septum-engaging portion of the swain tool is engaging the septum.

29. A method according to claim 28 wherein the septum has a bore extending part-way through the septum from the inside end of the septum; the step of inserting a pin into the passageway of the housing including inserting the pin into the bore of the septum.

30. A method of fabricating an injection or sampling site adapted to receive a blunt cannula, the method comprising the steps of:

providing a housing having an outside end and a passageway extending inwardly from the outside end, the passageway opening through the outside end and defining a longitudinal direction;

inserting an elastomeric septum into the passageway of the housing;

swaging the outside engage of the housing inwardly over the septum with a swaging tool, the swaging tool having a septum-engaging portion configured for directly engaging the septum before the swaged outside end of the housing applies longitudinal compression to the septum; and stopping the swaging process when the swaging tool applies a predetermined amount of force to the septum at the location where the septum-engaging portion of the swaging tool is engaging the septum;

the method further comprising cutting a slit into the septum before the septum is inserted into the passageway of the housing, the step of cutting a slit into the septum comprises:

providing an apparatus for slitting the septum comprising a block having a septum-receiving bore, a back support for supporting one end of the septum, and a knife;

inserting the septum into the septum-receiving bore against the back support;

cutting the slit into the septum; and removing the septum from the septum-receiving bore.

31. A method according to claim 20 wherein the back support has a passageway sized to allow the septum to be pushed through the passageway of the back support, the block being movable relative to the back support between a slitting station, in which the passageway of the back support is not adjacent the septum-receiving bore of the block, and an unloading station, in which the septum-receiving bore of the block is aligned with the passageway of the back support, the apparatus further comprising a pushing tool for pushing the septum out of the septum-receiving bore and through the passageway of the back support;

the step of removing the septum from the septum-receiving bore comprising:

moving the block to the unloading station; and pushing the septum out of the septum-receiving bore and through the passageway of the back support with the pushing tool.

32. A method according to claim 31 wherein the step of inserting the septum into the septum-receiving bore against the back support includes inserting the septum into the septum-receiving bore such that the inside end of the septum engages the back support;

the step of inserting the elastomeric septum into the passageway of the housing comprising:

aligning the passageway of the housing with the septum-receiving bore of the block and passageway of the back support, at the unloading station; and after the step of pushing the septum out of the septum-receiving bore, continuing to push the septum with the pushing tool into the passageway of the housing.

33. A method according to claim 30 wherein the back support has a knife-receiving opening, the step of cutting the slit into the septum comprising pushing the knife into the septum toward the knife-receiving opening.

34. A method of fabricating an injection or sampling site adapted to receive a blunt cannula, the method comprising the steps of:

providing a housing having an outside end and a passageway extending inwardly from the outside end, the passageway opening through the outside end and defining a longitudinal direction;

inserting an elastomeric septum into the passageway of the housing;

swaging the outside end of the housing inwardly over the septum with a swaging tool, the swaging tool having a septum-engaging portion configured for directly engaging the septum before the swaged outside end of the housing applies longitudinal compression to the septum; and stopping the swaging process when the swaging tool applies a predetermined amount of force to the septum at the location where the septum-engaging portion of the swaging tool is engaging the septum;

the septum-engaging portion and housing-swaging portion of the swaging tool being configured such that the septum-engaging portion of the swaging tool applies the predetermined force to the septum without the swaged outside end of the housing applying longitudinal compression to the septum; the step of stopping the swaging process comprising:

stopping the swaging process before the swaged outside end of the housing applies longitudinal compression to the septum.

35. A method of fabricating an injection or sampling site adapted to receive a blunt cannula, the method comprising the steps of:

providing a housing having an outside end and a passageway extending inwardly from the outside end, the passageway opening through the outside end and defining a longitudinal direction, the housing having an inner ledge defining the inner end of a septum-receiving portion of the passageway;

inserting an elastomeric septum into the passageway of the housing such that the inside end of the septum engages the inner ledge;

swaging the outside end of the housing inwardly over the septum with a swaging tool, the swaging tool having a septum-engaging portion configured for directly engaging the septum before the swaged outside end of the housing applies longitudinal compression to the septum; and stopping the swaging process when the swaging tool applies a predetermined amount of force to the septum at the location where the septum-engaging portion of the swaging tool is engaging the septum;

the septum-engaging portion and housing-swaging portion of the swaging tool being configured such that the septum-engaging portion of the swaging tool applies the predetermined force to the septum without the swaged outside end of the housing applying longitudinal compression to the septum; the step of stopping the swaging process comprising:

stopping the swaging process before the swaged outside end of the housing applies longitudinal compression to the septum, the swaged outside end of the housing defining an outer ledge defining the outer end of the septum-receiving portion of the passageway.

36. A method comprising:

providing an elastomeric septum;

providing an apparatus for slitting the septum comprising a block having a septum-receiving bore, a back support for supporting one end of the septum, and a knife;

inserting the septum into the septum-receiving bore against the back support, and constraining the septum in the septum-receiving bore against lateral deformation;

cutting the slit into the septum with the knife axially aligned with the septum-receiving bore;

after cutting the slit into the septum, removing the septum from the septum-receiving bore; and during or after removal of the septum from the septum-receiving bore, inserting the septum into a housing of an injection or sampling site.

37. A method according to claim 36 wherein the back support has a knife-receiving opening, the step of cutting the slit into the septum comprising pushing the knife into the septum toward the knife-receiving opening.

38. A method according to claim 36 wherein the back support has a passageway sized to allow the septum to be pushed through the passageway of the back support, the block being movable relative to the back support between a slitting station, in which the passageway of the back support is not adjacent the septum-receiving bore of the block, and an unloading station, in which the septum-receiving bore of the block is aligned with the passageway of the back support, the apparatus further comprising a pushing tool for pushing the septum out of the septum-receiving bore and through the passageway of the back support;

the step of removing the septum from the septum-receiving bore comprising:

moving the block to the unloading station; and pushing the septum out of the septum-receiving bore and through the passageway of the back support with the pushing tool.

39. A method according to claim 38 further comprising the step of inserting the septum into a passageway of a housing after the steps of slitting the septum and removing the septum from the septum-receiving bore.

40. A method according to claim 39 wherein the septum has an inside end and an outside end opposite the inside end; the step of inserting the septum into the septum-receiving bore against the back support including inserting the septum into the septum-receiving bore such that the inside end of the septum engages the back support;

the step of inserting the elastomeric septum into the passageway of the housing comprising:

aligning the passageway of the housing with the septum-receiving bore of the block and passageway of the back support; and after the step of pushing the septum out of the septum-receiving bore, continuing to push the septum with the pushing tool into the passageway of the housing.

41. A method according to claim 40 wherein the block comprises a turntable having a plurality of septum-receiving bores mounted for rotation relative to the back support to move the septum-receiving bores relative to back support between the slitting and unloading stations;

the step of moving the block to the unloading station comprising rotating the turntable to move one of the septum-receiving bores into alignment with the passageway of the back support.

42. A method according to claim 41 wherein the turntable constitutes a first turntable, a second rotatable turntable being provided having a plurality of housing-receiving openings for receiving the housing of the injection or sampling site, the second turntable being positioned such that one housing-receiving opening is aligned with the passageway of the back support and being rotatable to bring a next housing-receiving opening into alignment with the passageway of the back support;

the step of aligning the passageway of the housing with the septum-receiving bore of the block and passageway of the back support comprising rotating the second turntable to bring the next housing-receiving opening into alignment with the passageway of the back support as one of the septum-receiving bores is moved into alignment with the passageway of the back support.

43. A method according to claim 42 wherein the second turntable is rotatable to move the housing-receiving openings between a septum-loading station, in which a housing-receiving opening is aligned with the passageway of the back support, and a swaging station, in which the housing-receiving opening is aligned with a swaging tool for swaging an outside end of a housing located in that housing-receiving opening inwardly over a septum that was inserted into the passageway of the housing in the septum-loading station, the housing having an outside end and a passageway extending inwardly from the outside end, the passageway of the housing opening through the outside end and defining a longitudinal direction;

the method further comprising:
after inserting a septum into a housing located in a housing-receiving opening at the septum-loading station, rotating the second turntable to move the housing-receiving opening from the septum-loading station to the swaging station; and swaging, with the swaging tool, the outside end of the housing located in the housing-receiving opening that is at the swaging station inwardly over the septum inserted into the passageway of that housing.

44. A method according to claims 43 wherein the steps of cutting the slit into the septum, pushing the septum out of the septum-receiving bore and through the passageway of the back support, continuing to push the septum with the pushing tool into the passageway of the housing, and swaging the outside end of the housing inwardly over the septum are performed substantially simultaneously on different septums and housings positioned at the different stations.

45. A method according to claim 43 further comprising the steps of:
before or during the step of swaging the outside end of the housing inwardly over the septum, inserting a pin into the passageway of the housing to engage the inside end of the septum to reduce or prevent expansion of the septum inwardly through the passageway when the outer end of the housing is swaged;
during the step of swaging the outside end of the housing inwardly over the septum with the swaging tool, directly engaging the septum with a septum-engaging portion of the swaging tool; and
stopping the swaging process when the swaging tool applies a predetermined amount of force to the septum.

46. A method according to claim 45 wherein the septum has a bore extending part-way through the septum from the inside end of the septum; the step of inserting a pin into the passageway of the housing including inserting the pin into the bore of the septum.

47. A method according to claim 46 wherein the swaging tool has a septum-engaging portion and a housing-swaging portion, the step of stopping the swaging process further comprising engaging the septum with the septum-engaging portion of the swaging tool before stopping the swaging process.

48. A method according to claim 45 wherein the swaging tool has a septum-engaging portion and a housing-swaging portion, the step of stopping the swaging process further comprising engaging the septum with the septum-engaging portion of the swaging tool before stopping the swaging process.

49. A method according to claim 48 wherein the septum-engaging portion and housing-swaging portion of the swaging tool are configured such that the septum-engaging portion of the swaging tool applies the predetermined force to the septum without the swaged outside end of the housing applying longitudinal compression to the septum; the step of stopping the swaging process comprising:
stopping the swaging process before the swaged outside end of the housing applies longitudinal compression to the septum.

50. A method according to claim 45 wherein the housing has an inner ledge defining the inner end of a septum-receiving portion of the passageway; the step of inserting the septum into the passageway of the housing comprising inserting the septum into the passageway such that the inside end of the septum engages the inner ledge.

51. A method according to claim 50 wherein the septum has a bore extending part-way through the septum from the inside end of the septum; the step of inserting a pin into the passageway of the housing including inserting the pin into the bore of the septum.

52. A method according to claim 51 wherein the swaging tool has a septum-engaging portion and a housing-swaging portion, the step of stopping the swaging process further comprising engaging the septum with the septum-engaging portion of the swaging tool before stopping the swaging process.

53. A method according to claim 50 wherein the swaging tool has a septum-engaging portion and a housing-swaging portion, the step of stopping the swaging process further comprising engaging the septum with the septum-engaging portion of the swaging tool before stopping the swaging process.

54. A method according to claim 53 wherein the septum-engaging portion and housing-swaging portion of the swaging tool are configured such that the septum-engaging portion of the swaging tool applies the predetermined force to the septum without the swaged outside end of the housing applying longitudinal compression to the septum; the step of stopping the swaging process comprising:
stopping the swaging process before the swaged outside end of the housing applies longitudinal compression to the septum, the swaged outside end of the housing defining an outer ledge defining the outer end of the septum-receiving portion of the passageway.

* * * * *

UNITED STATES PATENT AND TRADEMARK OFFICE
CERTIFICATE OF CORRECTION

PATENT NO. : 5,351,383
DATED : October 4, 1994
INVENTOR(S) : Brett A. Behnke and Gary A. Thill It is certified that error appears in the above-indentified patent and that said Letters Patent is hereby corrected as shown below:

Col. 2, lines 35-36, "the a slit" should read --a slit--.

Col. 13, line 31, "provided facilitate" should read --provided to facilitate--.

Col. 17, line 1, "provide" should read --provided--.

Col. 21, line 5, "he" should read --the--.

Signed and Sealed this

Fourth Day of April, 1995

Attest:

BRUCE LEHMAN

Attesting Officer     Commissioner of Patents and Trademarks